(12) United States Patent
Lehman et al.

(10) Patent No.: US 8,652,151 B2
(45) Date of Patent: Feb. 18, 2014

(54) RIGHT ANGLE CLIP APPLIER APPARATUS AND METHOD

(75) Inventors: Adam Lehman, Wallingford, CT (US); Gene Stellon, Southington, CT (US); Ramiro Cabrera, Chesire, CT (US); Ralph A. Stearns, Bozrah, CT (US)

(73) Assignee: Covidien LP, Mansfield, MA (US)

( * ) Notice: Subject to any disclaimer, the term of this patent is extended or adjusted under 35 U.S.C. 154(b) by 140 days.

(21) Appl. No.: 13/006,073

(22) Filed: Jan. 13, 2011

(65) Prior Publication Data

US 2011/0112552 A1 May 12, 2011

Related U.S. Application Data

(63) Continuation of application No. 10/479,471, filed as application No. PCT/US02/21609 on Jul. 8, 2002, now Pat. No. 7,887,553.

(60) Provisional application No. 60/303,839, filed on Jul. 9, 2001.

(51) Int. Cl.
*A61B 17/10* (2006.01)

(52) U.S. Cl.
USPC ........................................................ 606/142

(58) Field of Classification Search
USPC ................. 606/142, 143, 139, 205, 208, 151; 227/902, 901, 175.4, 175.1, 176.1; 29/243.56; 53/138.4
See application file for complete search history.

(56) References Cited

U.S. PATENT DOCUMENTS

| | | | |
|---|---|---|---|
| 3,032,039 A | 5/1962 | Beaty |
| 3,056,408 A | 10/1962 | Brown |
| 3,098,232 A | 7/1963 | Brown |
| 3,363,628 A | 1/1968 | Wood |
| 3,446,212 A | 5/1969 | Le Roy |
| 3,604,425 A | 9/1971 | LeRoy |
| 3,631,707 A | 1/1972 | Miller |
| 3,882,854 A | 5/1975 | Hulka et al. |
| 3,958,576 A | 5/1976 | Komiya |
| 4,064,881 A | 12/1977 | Meredith |
| 4,170,990 A | 10/1979 | Baumgart et al. |
| 4,217,902 A | 8/1980 | March |
| 4,274,415 A | 6/1981 | Kanamoto et al. |
| 4,317,451 A | 3/1982 | Cerwin et al. |
| 4,396,139 A | 8/1983 | Hall et al. |

(Continued)

FOREIGN PATENT DOCUMENTS

| | | |
|---|---|---|
| DE | 2730691 A1 | 1/1978 |
| DE | 4015562 A1 | 11/1991 |

(Continued)

*Primary Examiner* — Victor Nguyen
*Assistant Examiner* — Jocelin Tanner

(57) ABSTRACT

A right angle clip applier apparatus including a distal clip applying mechanism and a proximal advancing mechanism positioned in a handle assembly. The clip applying mechanism includes a feed rod interfacing with a cartridge for the advancing and applying of clips on tissue portions. A plurality of clips are enclosed in the apparatus. The advancing mechanism is actuated by a lever in the handle assembly which creates a drive force that repositions the feed rod and clips. Each actuation of the lever applies a first clip and advances clips to a new position in a distal direction. The clip applying mechanism can be utilized at any angle and can be rotated through 360 degrees while holding the handle in a fixed position. An empty clip indicator is provided.

23 Claims, 21 Drawing Sheets

(56) References Cited

U.S. PATENT DOCUMENTS

| | | | |
|---|---|---|---|
| 4,402,445 | A | 9/1983 | Green |
| 4,418,694 | A | 12/1983 | Beroff et al. |
| 4,433,689 | A | 2/1984 | von Zeppelin |
| 4,444,187 | A | 4/1984 | Perlin |
| 4,471,780 | A * | 9/1984 | Menges et al. .............. 606/143 |
| 4,476,865 | A | 10/1984 | Failla et al. |
| 4,484,581 | A | 11/1984 | Martin et al. |
| 4,485,816 | A | 12/1984 | Krumme |
| 4,492,232 | A | 1/1985 | Green |
| 4,506,670 | A | 3/1985 | Crossley |
| 4,512,345 | A | 4/1985 | Green |
| 4,513,746 | A | 4/1985 | Aranyi et al. |
| 4,527,562 | A | 7/1985 | Mericle |
| 4,534,350 | A | 8/1985 | Golden et al. |
| 4,534,352 | A | 8/1985 | Korthoff |
| 4,579,118 | A | 4/1986 | Failla |
| 4,590,937 | A | 5/1986 | Deniega |
| 4,610,250 | A | 9/1986 | Green |
| 4,612,932 | A | 9/1986 | Caspar et al. |
| 4,616,651 | A | 10/1986 | Golden |
| 4,620,541 | A | 11/1986 | Gertzman et al. |
| 4,638,804 | A | 1/1987 | Jewusiak |
| 4,646,741 | A | 3/1987 | Smith |
| 4,658,822 | A | 4/1987 | Kees, Jr. |
| 4,660,558 | A | 4/1987 | Kees, Jr. |
| 4,667,674 | A | 5/1987 | Korthoff et al. |
| 4,671,278 | A | 6/1987 | Chin |
| 4,696,396 | A | 9/1987 | Samuels |
| 4,702,247 | A | 10/1987 | Blake et al. |
| 4,741,337 | A | 5/1988 | Smith et al. |
| 4,765,335 | A | 8/1988 | Schmidt et al. |
| 4,777,949 | A | 10/1988 | Perlin |
| 4,777,950 | A | 10/1988 | Kees, Jr. |
| 4,791,707 | A | 12/1988 | Tucker |
| 4,796,625 | A | 1/1989 | Kees, Jr. |
| 4,796,627 | A | 1/1989 | Tucker |
| 4,799,481 | A | 1/1989 | Transue et al. |
| 4,805,617 | A | 2/1989 | Bedi et al. |
| 4,805,618 | A | 2/1989 | Ueda et al. |
| 4,822,348 | A | 4/1989 | Casey |
| 4,834,096 | A | 5/1989 | Oh et al. |
| 4,844,066 | A | 7/1989 | Stein |
| 4,932,960 | A | 6/1990 | Green et al. |
| 4,950,258 | A | 8/1990 | Kawai et al. |
| 4,951,860 | A | 8/1990 | Peters et al. |
| 4,957,500 | A | 9/1990 | Liang et al. |
| 4,961,743 | A | 10/1990 | Kees, Jr. et al. |
| 4,966,603 | A | 10/1990 | Focelle et al. |
| 4,972,949 | A | 11/1990 | Peiffer |
| 4,976,722 | A | 12/1990 | Failla |
| 4,983,176 | A | 1/1991 | Cushman et al. |
| 5,002,552 | A | 3/1991 | Casey |
| 5,002,563 | A | 3/1991 | Pyka et al. |
| 5,035,692 | A | 7/1991 | Lyon et al. |
| 5,044,540 | A | 9/1991 | Dulebohn |
| 5,053,045 | A | 10/1991 | Schmidt et al. |
| 5,057,118 | A | 10/1991 | Picha |
| 5,062,846 | A | 11/1991 | Oh et al. |
| 5,062,848 | A | 11/1991 | Frazee et al. |
| 5,089,009 | A | 2/1992 | Green |
| 5,160,339 | A | 11/1992 | Chen et al. |
| 5,171,250 | A | 12/1992 | Yoon |
| 5,171,251 | A | 12/1992 | Bregen et al. |
| 5,192,288 | A | 3/1993 | Thompson et al. |
| 5,201,746 | A | 4/1993 | Shichman |
| 5,207,692 | A | 5/1993 | Kraus et al. |
| 5,217,472 | A | 6/1993 | Green et al. |
| 5,217,473 | A | 6/1993 | Yoon |
| 5,219,353 | A | 6/1993 | Garvey, III et al. |
| 5,222,961 | A | 6/1993 | Nakao et al. |
| 5,234,449 | A | 8/1993 | Bruker et al. |
| 5,236,435 | A | 8/1993 | Sewell, Jr. |
| 5,242,456 | A | 9/1993 | Nash et al. |
| 5,257,713 | A | 11/1993 | Green et al. |
| 5,269,792 | A | 12/1993 | Kovac et al. |
| 5,282,808 | A * | 2/1994 | Kovac et al. .................. 606/143 |
| 5,282,812 | A | 2/1994 | Suarez, Jr. |
| 5,289,963 | A | 3/1994 | McGarry et al. |
| 5,290,299 | A | 3/1994 | Fain et al. |
| 5,306,280 | A | 4/1994 | Bregen et al. |
| 5,312,426 | A | 5/1994 | Segawa et al. |
| 5,330,442 | A | 7/1994 | Green et al. |
| 5,342,373 | A | 8/1994 | Stefanchik et al. |
| 5,354,306 | A | 10/1994 | Garvey, III et al. |
| 5,366,458 | A | 11/1994 | Korthoff et al. |
| 5,366,459 | A | 11/1994 | Yoon |
| 5,366,479 | A | 11/1994 | McGarry et al. |
| 5,381,943 | A | 1/1995 | Allen et al. |
| 5,425,740 | A | 6/1995 | Hutchinson, Jr. |
| 5,431,667 | A * | 7/1995 | Thompson et al. ........... 606/142 |
| 5,441,509 | A | 8/1995 | Vidal et al. |
| 5,464,416 | A | 11/1995 | Steckel |
| 5,474,567 | A | 12/1995 | Stefanchik et al. |
| 5,487,746 | A | 1/1996 | Yu et al. |
| 5,497,933 | A | 3/1996 | DeFonzo et al. |
| 5,520,701 | A | 5/1996 | Lerch |
| 5,540,704 | A | 7/1996 | Gordon et al. |
| 5,547,474 | A | 8/1996 | Kloeckl et al. |
| 5,569,274 | A | 10/1996 | Rapacki et al. |
| 5,571,121 | A | 11/1996 | Heifetz |
| 5,593,414 | A | 1/1997 | Shipp et al. |
| 5,601,573 | A | 2/1997 | Fogelberg et al. |
| 5,601,574 | A | 2/1997 | Stefanchik et al. |
| 5,618,291 | A | 4/1997 | Thompson et al. |
| 5,632,753 | A | 5/1997 | Loeser |
| RE35,525 | E | 6/1997 | Stefanchik et al. |
| 5,634,932 | A | 6/1997 | Schmidt |
| 5,643,291 | A * | 7/1997 | Pier et al. ...................... 606/143 |
| 5,681,330 | A | 10/1997 | Hughett et al. |
| 5,683,405 | A | 11/1997 | Yacoubian et al. |
| 5,695,505 | A | 12/1997 | Yoon |
| 5,713,911 | A | 2/1998 | Racenet et al. |
| 5,725,542 | A | 3/1998 | Yoon |
| 5,741,277 | A | 4/1998 | Gordon et al. |
| 5,758,420 | A | 6/1998 | Schmidt et al. |
| 5,766,189 | A | 6/1998 | Matsuno |
| 5,769,857 | A | 6/1998 | Reztzov et al. |
| 5,827,306 | A | 10/1998 | Yoon |
| 5,833,700 | A | 11/1998 | Fogelberg et al. |
| 5,843,101 | A | 12/1998 | Fry |
| 5,849,019 | A | 12/1998 | Yoon |
| 5,858,018 | A | 1/1999 | Shipp et al. |
| 5,921,997 | A | 7/1999 | Fogelberg et al. |
| 5,941,890 | A | 8/1999 | Voegele et al. |
| 6,015,417 | A | 1/2000 | Reynolds, Jr. |
| 6,059,799 | A | 5/2000 | Aranyi et al. |
| 6,179,850 | B1 | 1/2001 | Goradia |
| 6,193,732 | B1 | 2/2001 | Frantzen et al. |
| 6,193,733 | B1 | 2/2001 | Adams |
| 6,206,897 | B1 | 3/2001 | Jamiolkowski et al. |
| 6,210,418 | B1 | 4/2001 | Storz et al. |
| 6,273,903 | B1 | 8/2001 | Wilk |
| 6,346,112 | B2 | 2/2002 | Adams |
| 6,419,682 | B1 | 7/2002 | Appleby et al. |
| 6,824,547 | B2 | 11/2004 | Wilson et al. |
| 6,877,647 | B2 | 4/2005 | Green et al. |

FOREIGN PATENT DOCUMENTS

| | | |
|---|---|---|
| EP | 0490411 A1 | 6/1992 |
| EP | 0592000 A2 | 4/1994 |
| EP | 0609612 A2 | 8/1994 |
| WO | WO88/01486 | 3/1988 |
| WO | WO88/01487 A1 | 3/1988 |
| WO | WO 93/24059 A2 | 12/1993 |
| WO | WO95/05778 A1 | 3/1995 |

* cited by examiner

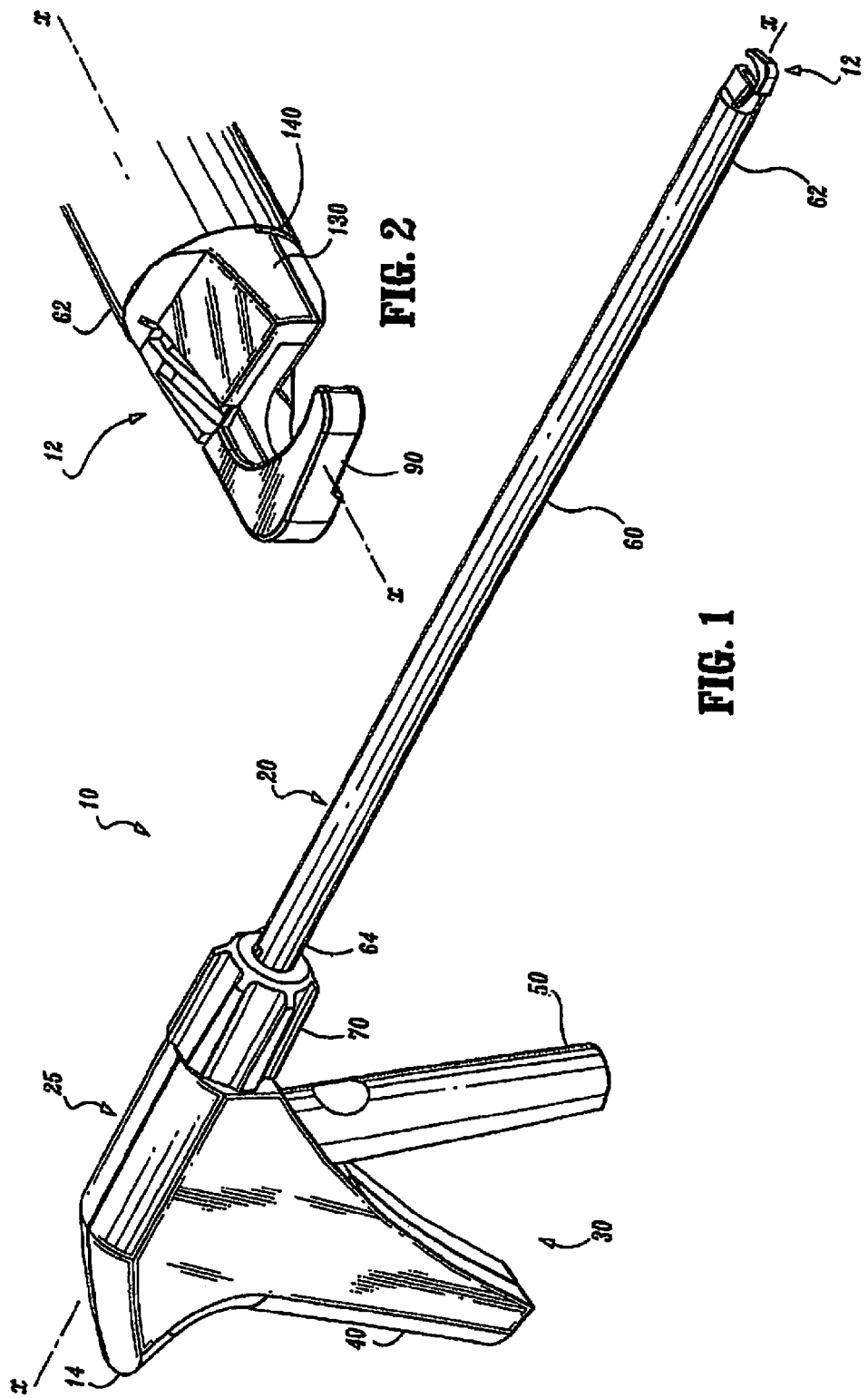

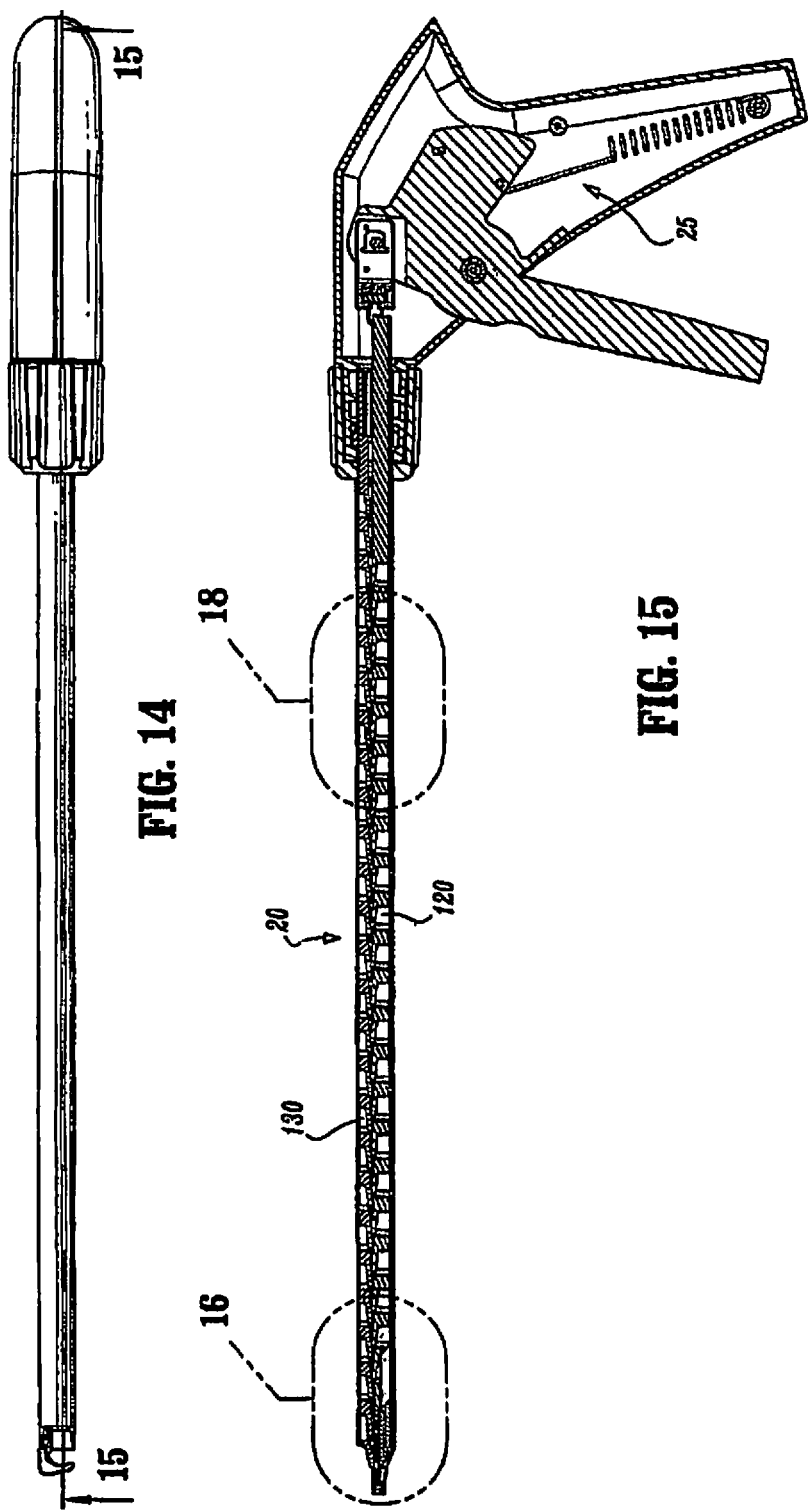

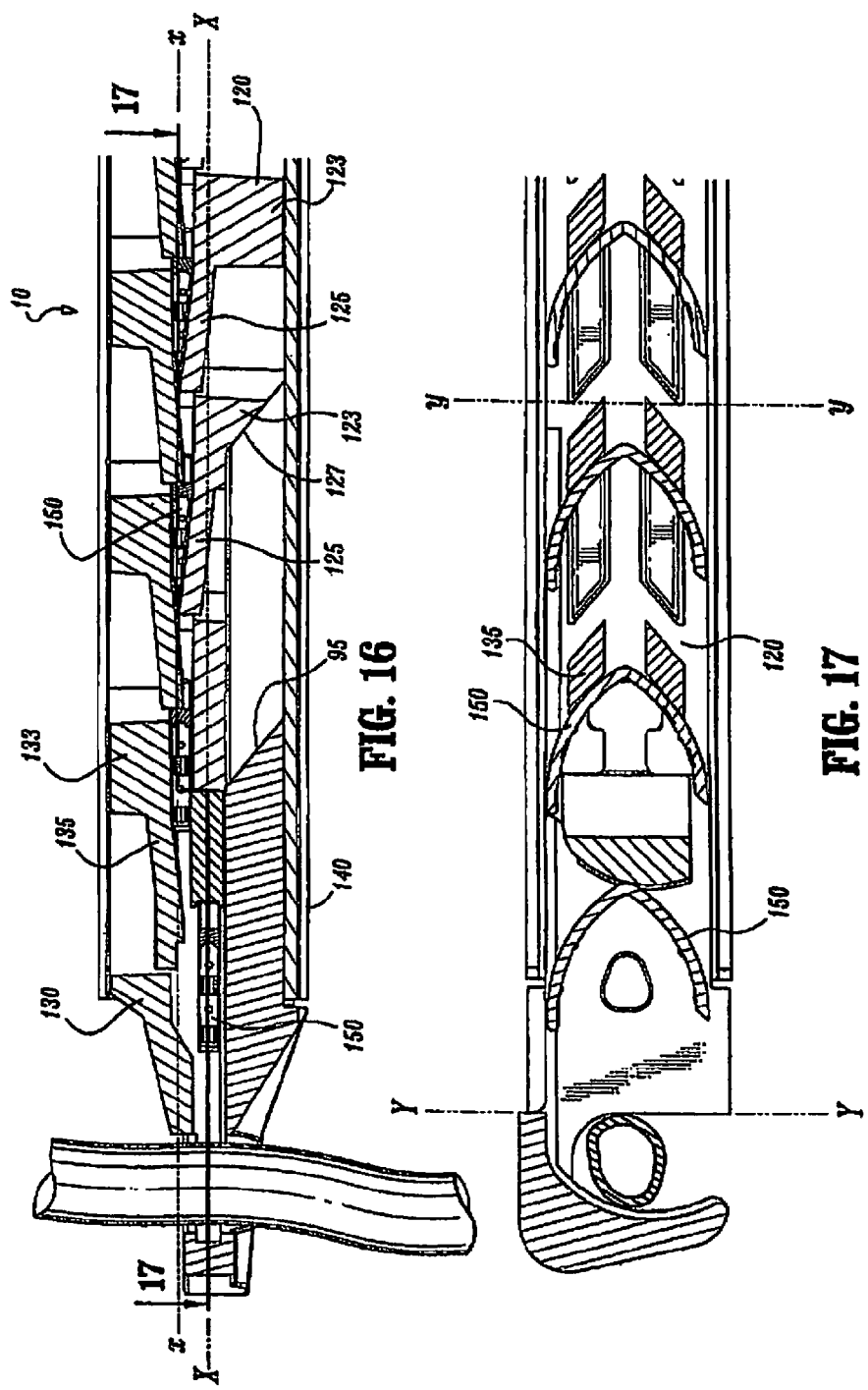

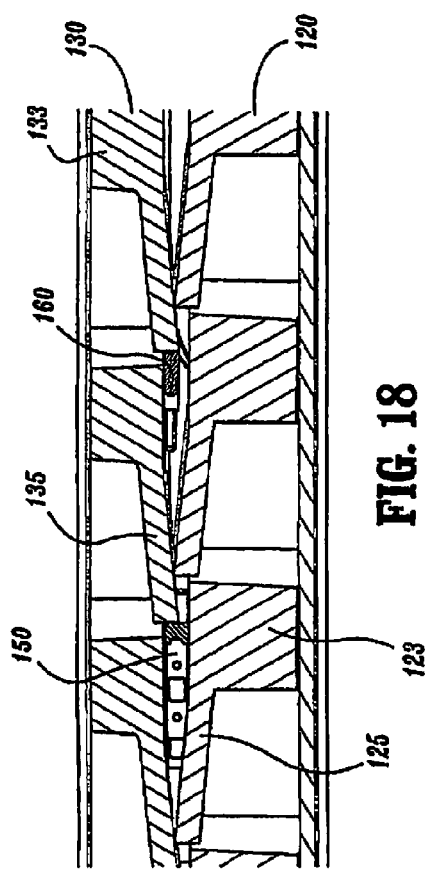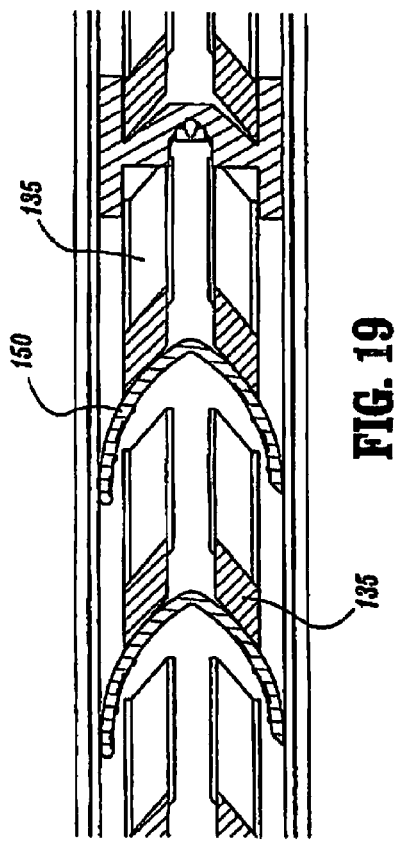

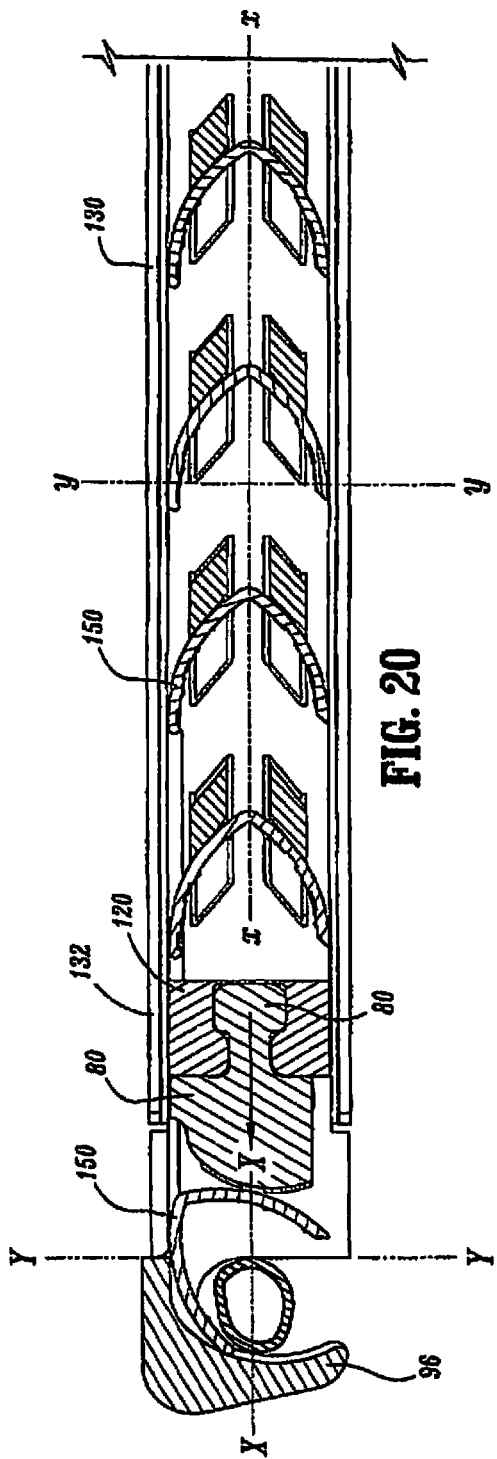
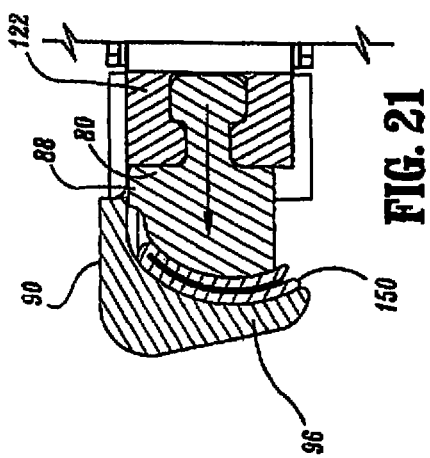

RIGHT ANGLE CLIP APPLIER APPARATUS AND METHOD

CROSS-REFERENCE TO RELATED APPLICATIONS

This application is a continuation of U.S. patent application Ser. No. 10/479,471, filed on Dec. 2, 2003, which is a National Stage Entry of International Patent Application No. PCT/US02/21609, filed Jul. 8, 2002, which claims the benefit of, and priority to, U.S. Provisional Patent Application Ser. No. 60/303,839, filed on Jul. 9, 2001, the entire contents of each application being incorporated by reference herein in its entirety.

BACKGROUND

1. Technical Field

The present disclosure relates to a clip applying apparatus. More particularly, the present disclosure relates to an apparatus for applying clips in surgical procedures.

2. Background of the Related Art

Clip applying apparatuses or clip applicators are used in laparoscopic or endoscopic surgery and include single clip applicators and multiple clip applicators.

Single clip applicators can be time consuming to use, but are relatively low cost instruments due to their simplicity and ability to be sterilized and reused. Multiple clip applicators have complex internal mechanisms for advancing and applying clips that limit their ability to be sterilized as well as undesirably increasing designing and manufacturing costs. Thus, multiple clip applicators are commonly employed surgical devices that are relatively costly disposable items.

An additional problem with clip applying apparatuses is encountered during the confines of endoscopic surgery during the clip applying process. Clip applying apparatuses that apply clips in axial alignment with the longitudinal axis typically have sufficient structure within the trocar to hamper the ability of the surgeon to see the exact point where the clip is applied.

A continuing need exists for a multiple clip applying apparatus utilizing a simplified low cost advancing and clip applying mechanism in a right angled applicator that accommodates improved visibility during the application of clips.

SUMMARY

A right angle clip applying apparatus is provided including a handle assembly for actuating an advancing mechanism that is connected with a clip applying mechanism. The clip applying mechanism is rotatable about a longitudinal axis independent of the handle assembly and includes a cartridge, a feed rod, and an anvil channel. The movable feed rod includes a hammer and is slidingly engaged with the cartridge and anvil channel. The feed rod includes a plurality of elements for distally advancing a plurality of clips positioned thereon. The anvil channel includes an anvil positioned perpendicular to the central longitudinal axis and configured to apply a clip advanced by the hammer.

A method for applying clips at a right angle includes advancing a plurality of clips in a first position in a distal direction in a clip applying mechanism by actuating a drive mechanism. The plurality of clips including a first clip that when advanced rotates approximately 90 degrees and is applied on the tissue by compressing portions of the clip together on a tissue portion.

The invention, together with attendant advantages, will be best understood by reference to the following detailed description of the invention when used in conjunction with the figures below.

BRIEF DESCRIPTION OF THE DRAWINGS

Preferred embodiments of the presently disclosed right angle clip applying apparatus are described herein with reference to the drawings, wherein:

FIG. 1 is an isometric view of a right angle clip applier apparatus constructed in accordance with the present disclosure;

FIG. 2 is a close-up isometric view of a distal end portion of the apparatus of FIG. 1;

FIG. 14 is a top view of the apparatus of FIG. 1;

FIG. 15 is a cross-sectional view of FIG. 14 along section line 15-15;

FIG. 16 is an enlarged view of the indicated area of detail identified in FIG. 15, which shows a tubular vessel positioned in the anvil portion;

FIG. 17 is a cross-sectional top view of FIG. 16 along section line 17-17 illustrating the clips in a distal end portion of the feed rod;

FIG. 18 is an enlarged view of the indicated area of detail identified in FIG. 15;

FIG. 19 is a cross-sectional top view of a portion of the apparatus of FIG. 1 illustrating the clips positioned between the feed rod and the cartridge;

FIG. 20 is a cross-sectional top view of a portion of the feed rod of the apparatus of FIG. 1 illustrating the rotating of a first clip for compression between the hammer and anvil and the advancement of subsequent clips in the series;

FIG. 21 is a cross-sectional top view of the anvil and hammer of FIG. 20 in the closed position with a clip compressed to a closed configuration therein;

DETAILED DESCRIPTION OF PREFERRED EMBODIMENTS

Figure 3:
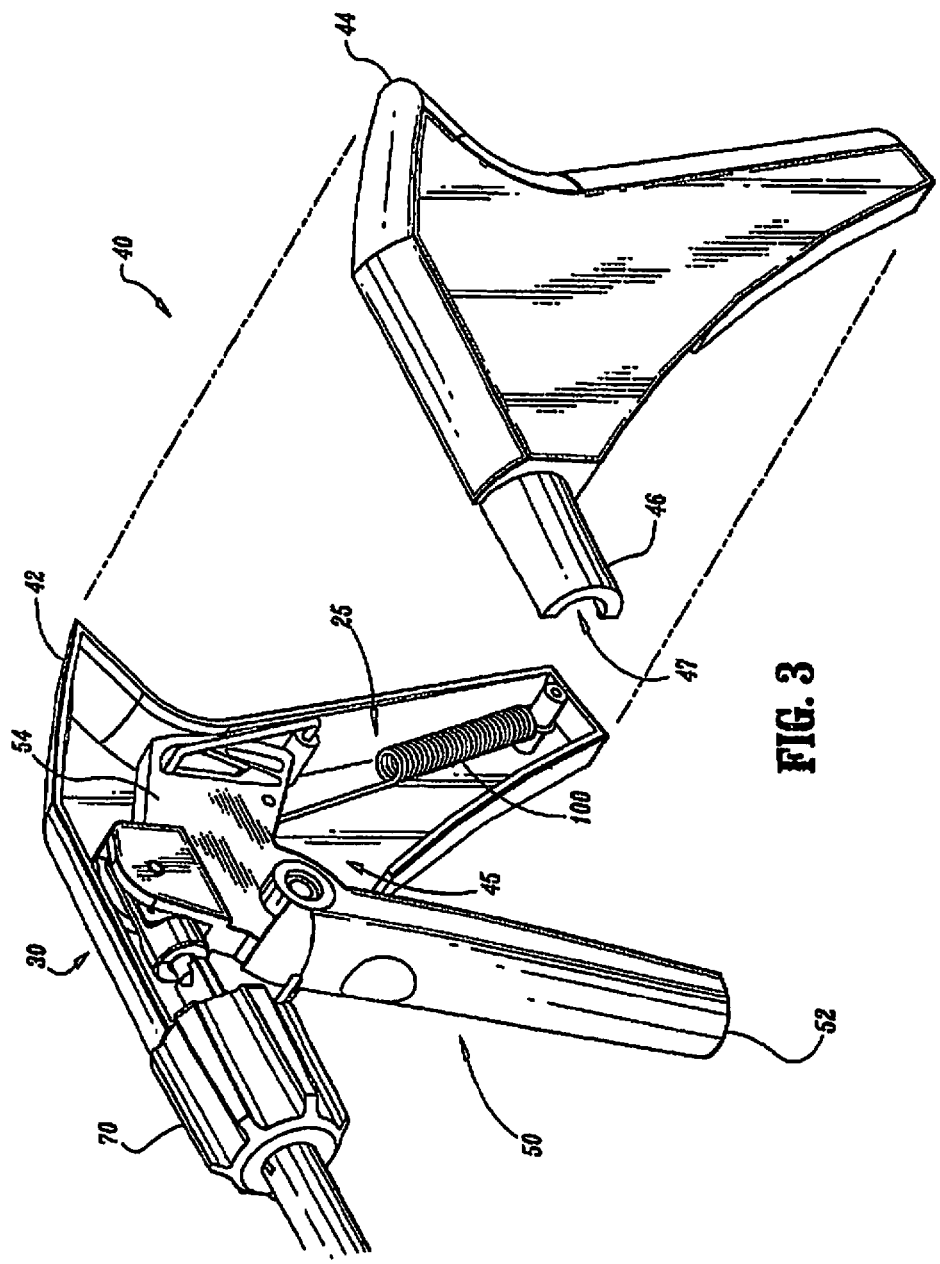
FIG. 3 is an exploded isometric view of a proximal end portion of the apparatus of FIG. 1.

Referring now in specific detail to the drawings in which like referenced numerals identify similar or identical elements throughout the several views and initially to FIG. 1, wherein a preferred embodiment of a right angle clip applier apparatus 10 is illustrated having a distal end portion 12 and a proximal end portion 14. Distal end 12 includes a portion of a clip applying mechanism 20. An outer tubular sleeve 60 has a distal end 62 and a proximal end 64 positioned with a rotation control knob 70. A central longitudinal axis of apparatus 10 is designated by the dashed line X-X. Proximal end portion 14 includes a handle assembly 30. Handle assembly 30 has a grip 40 and a lever 50 enclosing an advancing mechanism disposed within the housing at a region indicated by reference numeral 25.

Apparatus 10 may be made from any suitable medical grade materials, for example, plastic or metal materials approved for use in medical instrumentation.

In FIG. 2, distal end portion 12 is shown with distal end 62 in sleeve 60 positioned over a cartridge 130 and an anvil channel 140. In one preferred embodiment, an anvil 90 is positioned perpendicular to the central longitudinal axis "X-X" and clips 150 (FIG. 5) are applied after having been rotated approximately 90.degree. from the central longitudinal axis "X-X". This angle allows for improved visibility of the tissue portion to be clipped. It is contemplated that distal end 12, however, could be configured and dimensioned to apply clips at any angle distinct from the central longitudinal axis.

Referring now to FIG. 3, handle 30 includes a grip 40 having a first grip portion 42 and a second grip portion 44, which in conjunction with lever 50, house advancing mechanism 25. Lever 50 includes a distal end portion 52 configured as a trigger for at least one finger to grip and a proximal portion 54 positioned inside grip 40. Grip 40 defines a hole 45 between first grip portion 42 and second grip portion 44 for the positioning of lever 50. Grip portions 42 and 44 include partially tubular shaped portions 46 with at least one partially cylindrical shaped recess 47 defined therein. Rotation control knob 70 at least partially secures grip portions 42 and 44 of handle 30 in a locked position.

Figure 4:
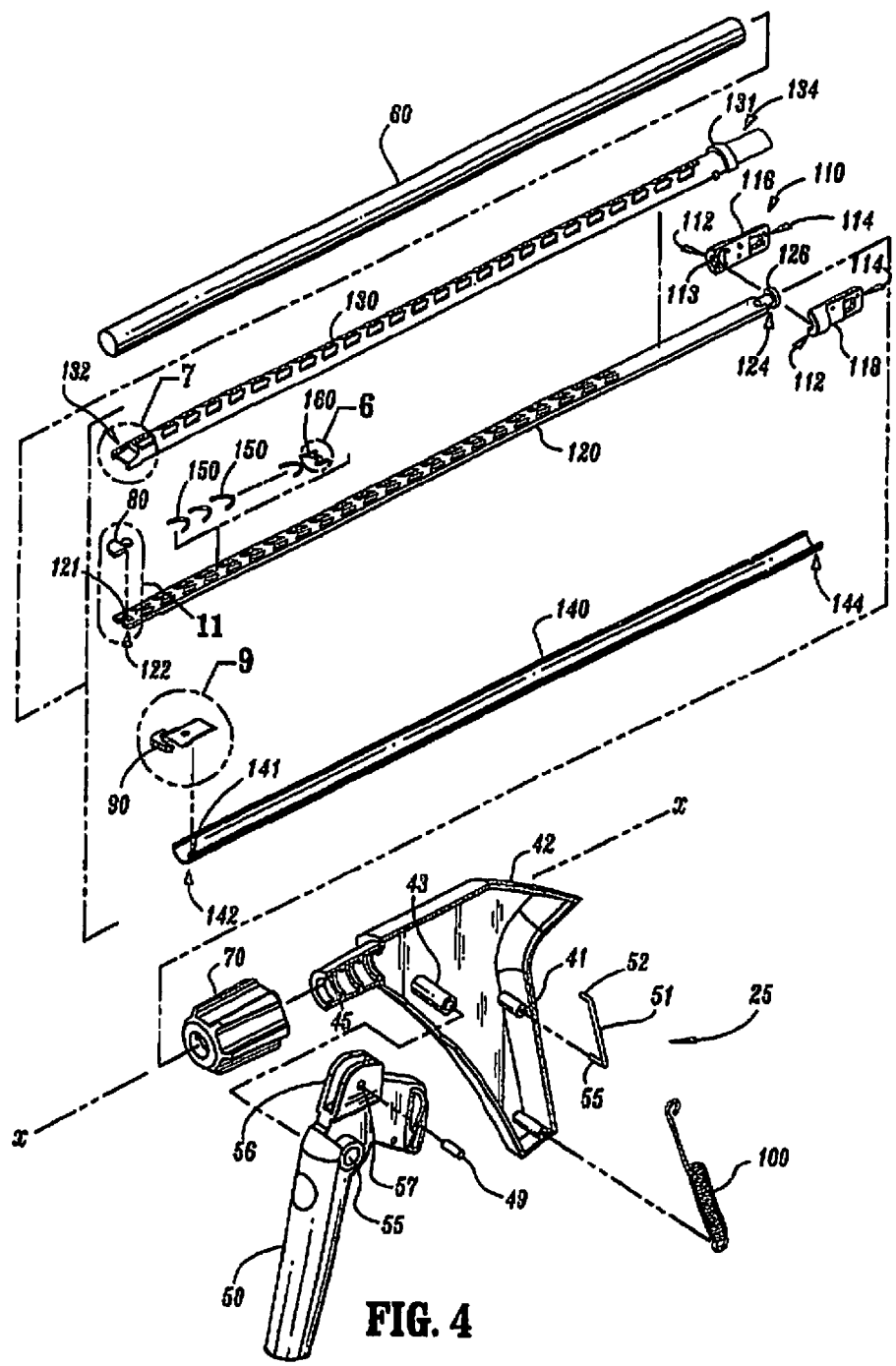
FIG. 4 is an exploded isometric view of the apparatus of FIG. 1.

As shown in FIG. 4, one preferred embodiment of advancing mechanism 25 is illustrated in a first position wherein lever 50 is fully extended in the distal direction. Lever 50 is mounted through a hole 55 defined therein on pin 43 of first grip portion 42. Pin 43 acts as a pivot for lever 50. Lever 50 pivots between the first position and a second position wherein in the second position lever 50 is moved in a proximal direction to the vicinity of grip 40. The range of movement of lever 50 is at least partially controlled by a hook 51 configured as a wire with two cantilevered arms which provide a controlled amount of bias as well as a portion of the limiting force for the range of movement of lever 50. Hook 57 has a first end 52 positioned in a slot 41 defined in proximal end 44 and a second end 55 positioned in a hole 41 defined in first grip portion 42.

A bias member such as spring 100 is positioned in first grip portion 42 that provides a force directed to position lever 50 in the first position. Lever 50 also includes a bracket 56 for the positioning of a swivel 110. Swivel 110 defines a hole 111 and bracket 56 defines a hole 57 through which load pin 49 is positioned to pivotally lock swivel 110 in position on lever 50.

Swivel 110 has a distal end portion 112 and a proximal end portion 114. Swivel 110 is further defined as having a first portion 116 and a second portion 118. First portion 116 and second portion 118 are longitudinally separated portions that mate together to form swivel 110. Distal end portion 112 defines a cylindrical shaped recess 113 for a flange 126 positioned on a proximal end portion 124 of feed rod 120. Swivel 110 transfers the drive force from lever 50 to translate feed rod 120 along the central longitudinal axis "X-X". In addition, cylindrical recess 113 in swivel 110 accommodates the rotation of feed rod 120 and the other portions of clip applying mechanism 20 about the central longitudinal axis.

Clip applying mechanism 20 includes outer tube 60, rotation control knob 70, cartridge 130, feed rod 120, a hammer 80, anvil channel 140, and anvil 90. Outer tube 60 may be formed from a layer of plastic suitable for surgical applications and is preferably shrink wrapped into position thereby securing cartridge 130 and anvil channel 140 in apposition with feed rod 120. Outer tube 60, cartridge 130 and anvil channel 140 are fixed in position relative to the translation of feed rod 120 distally and proximally along longitudinal axis "X-X", but rotate with feed rod 120 and rotation control knob 70 about longitudinal axis "X-X".

Feed rod 120 includes a distal end 122 defining a slot 121 for cooperatively mating with a tabular portion 81 of hammer 80. Hammer 80 is positioned to translate and cooperatively engage with anvil 90 positioned on anvil channel 140. Anvil channel 140 has an arcuate cross-section and includes a distal end portion 142 and a proximal end portion 144. Anvil channel 140 is preferably made of a medical grade metal, but could be made from medical grade plastics or composite materials of suitable structural integrity.

Anvil channel 140 and cartridge 130 are configured to form a cylindrical tube having an outside first circumference with feed rod 120 positioned therein. Proximal end portion 134 includes a cylindrical portion 131 having a second outside circumference greater than the first outside circumference that cooperatively engages with one of the at least one cylindrical recesses 45 in grip portions 42 and 44 (not shown). The engagement of cylindrical portion 131 with recess 45 fixes cartridge 130 and anvil channel 140 from translating along the longitudinal axis "X-X" and accommodates rotation of the feed rod 120, cartridge 130 and anvil channel 140 with rotation control knob 70.

Feed rod 120 and cartridge 130 are cooperatively engaged with a plurality of clips 150 positioned therein for the advancing and applying of each clip 150. Cartridge 130 has a distal end 132 that functions to assist distal end portion 122 in the positioning and applying of clips 150 between anvil 90 and hammer 80. Proximal to the most proximal clip 150 is an empty clip indicator 160.

Right angle clip applier apparatus 10 is preferably configured as a disposable item with a plurality of clips 150 pre-positioned therein. Alternatively, however, apparatus 10 may also be configured with a removable and replaceable subassembly, such as clip applying mechanism 20, for loading and applying a plurality of clips 150.

Figure 5:
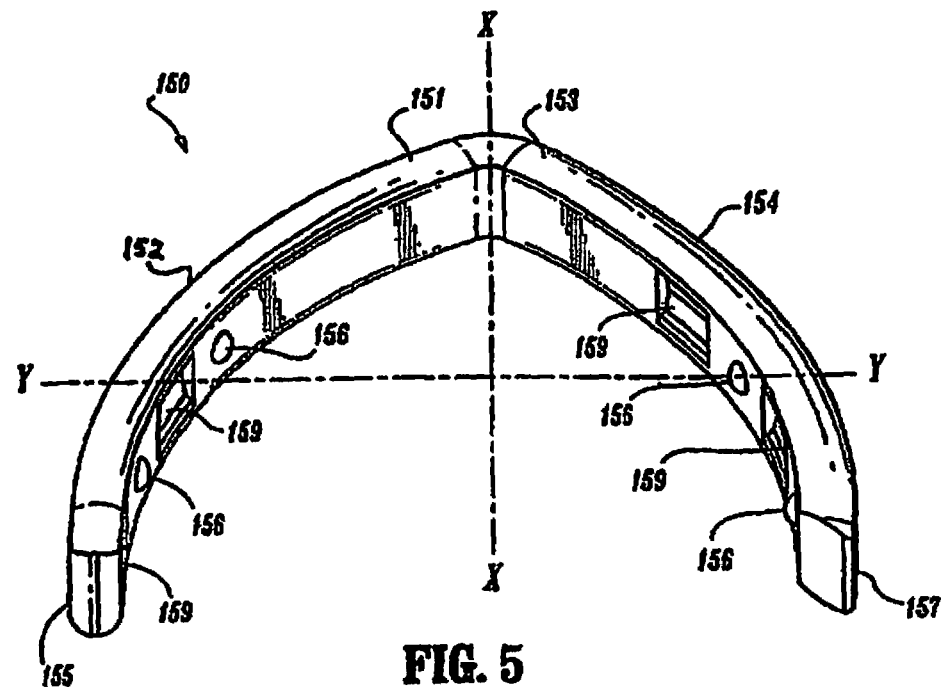
FIG. 5 is an isometric view of one configuration of a clip constructed in accordance with the present disclosure.

Referring now to FIG. 5, clip 150 in one preferred embodiment includes a first leg 152 and a second leg 154. Legs 152 and 154 have a generally arcuate shape and are joined together at their respective proximal end portions 151 and 153. Leg 152 has a distal end 155 with a blunt rounded tip and at least one recess 159 defined on the inside of each leg. Leg 154 has at least one recess 159 and distal end 157 has a beveled tip. The inside portions of legs 152 and 154 also include at least one protuberance 156. Leg 152 is slightly longer than leg 154 in one preferred configuration.

Clip 150 is crimped along the axis "Y-Y" when positioned between hammer 80 and anvil 90 and the mating of at least one protuberance 156 with at least one recess 159 provides greater adhesion with tissue portion being clipped. At least one protuberance 156 is shown as approximately hemispherical, but it could take any geometric shape, such as a needle tip or pyramid, depending upon the application. Legs 152 and 154 extend in the general direction of the "X-X" axis. Right angle clip applier apparatus 10 is configured to function utilizing a variety of clips with varying geometric forms. Additional configurations may include, but are not limited to clips with extended length legs, linear legs, clips with legs that have both linear and arcuate portions, as well as clips having at least two legs with at least one leg forming a clip having an increased dimension or configuration in a plane perpendicular to the axes "X-X" and "Y-Y". Clips 150 are preferably made from a titanium composition.

Figure 6:
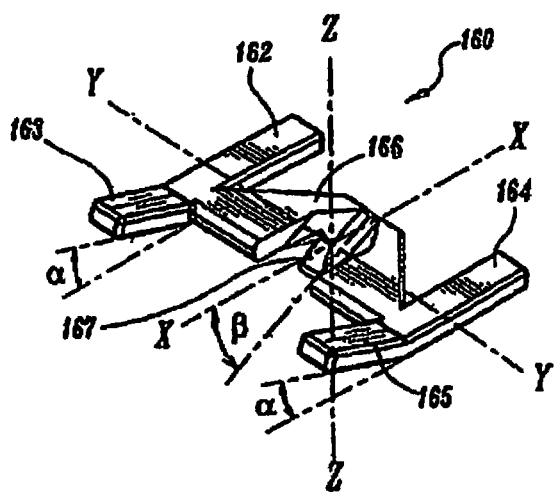
FIG. 6 is an isometric view of an empty clip indicator constructed in accordance with the present disclosure.

In FIG. 6, an empty clip indicator 160 has two linear legs 162 and 164 parallel to an axis "X-X" connected by a cross member 166 parallel to an axis "Y-Y". Legs 162 and 164 have portions 163 and 165 respectively which are at an angle "a" from the longitudinal axis "X-X". Cross member 166 includes a cantilevered portion 167 extending distally at an angle ".beta." from the longitudinal axis "X-X" that has a generally concave shape within indicator 160. Portion 167 and portions 163 and 165 both extend distally and in opposing directions in an axis "Z-Z", perpendicular to the axes "X-X" and "Y-Y".

Empty clip indicator 160 and clips 150 feed in the direction of their respective axes "X-X", with clips 150 being disposed in a first position with an open end oriented distally through right angle clip applier apparatus 10 until being urged to a first or distal most clip position. In one preferred embodiment, the failure of empty clip indicators 160 to rotate into anvil 90 also blocks the actuation of lever 50. Thus, an indication that right angle clip applier apparatus 10 has exhausted the plurality of clips 150 positioned in cartridge 130 is provided by empty clip indicator 160 within clip applying mechanism 20.

Figure 7:
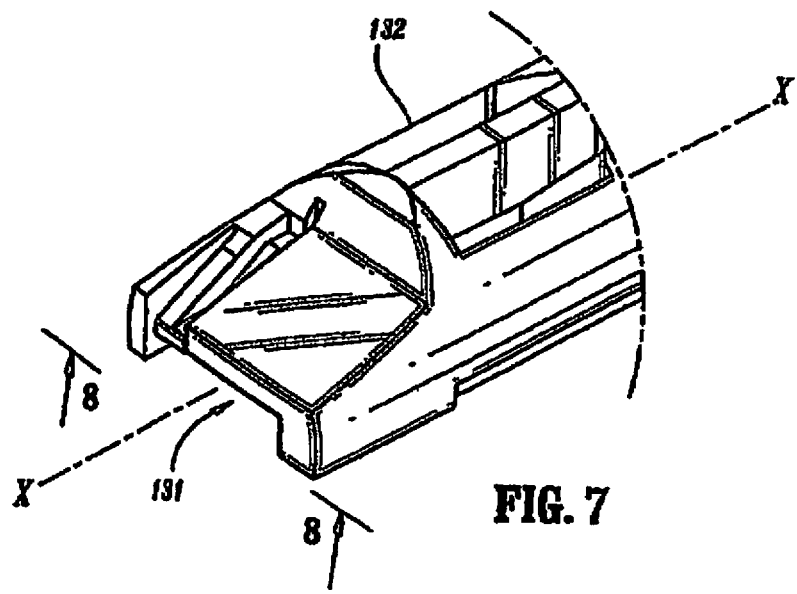
FIG. 7 is an isometric view of a distal end portion of a cartridge of the apparatus of FIG. 1.
Figure 8:
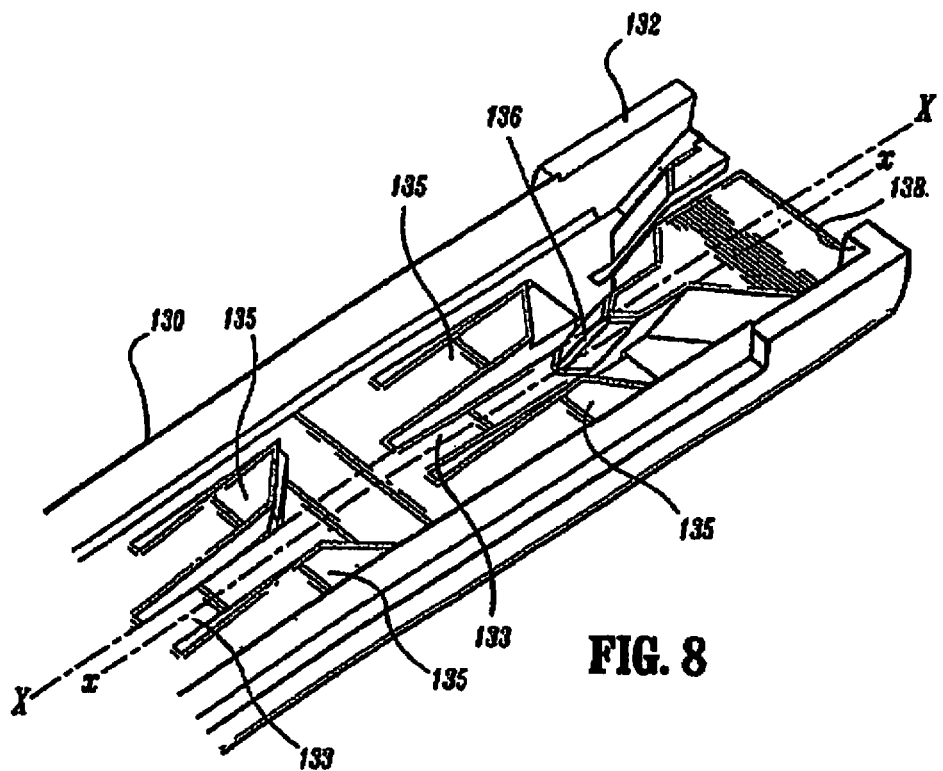
FIG. 8 is an isometric view of the distal end portion of the cartridge of FIG. 7 viewed along line 8-8.

In FIGS. 4, 7, and 8 distal end 132 is shown defining a slot 131 transverse to the central longitudinal axis "X-X" to permit the distal passage of clips 150. Distal end 132 includes a ramp portion 136 and a stop portion 138. Cartridge 130 includes a plurality of elements 133 for engaging and retaining clips 150 in position after being forwarded distally by the forward translation of feed rod 120.

In a preferred embodiment, elements 133 are formed as portions of cartridge 130 with a pair of cantilevered and flexible beams 135 at least partially shaped to correspond with a portion of the clips 150. Clips 150 feed along a plane defined by the interface between feed rod 120 and end cartridge 130 defining an axis "x-x" parallel to central longitudinal axis "X-X" and perpendicular to an axis "y-y". Ramp 136 formed in distal end portion 132 and stop 138 assist in repositioning clips 150 to a plane formed by axes "X-X" "Y-Y", parallel to a plane "x-y".

Figure 9:
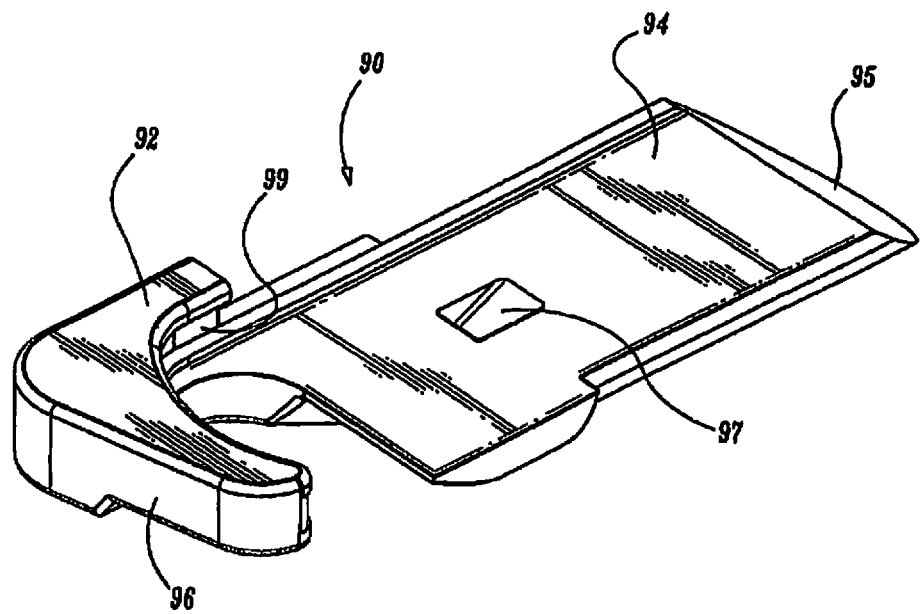
FIG. 9 is an isometric top view of an anvil of the apparatus of FIG. 1.
Figure 10:
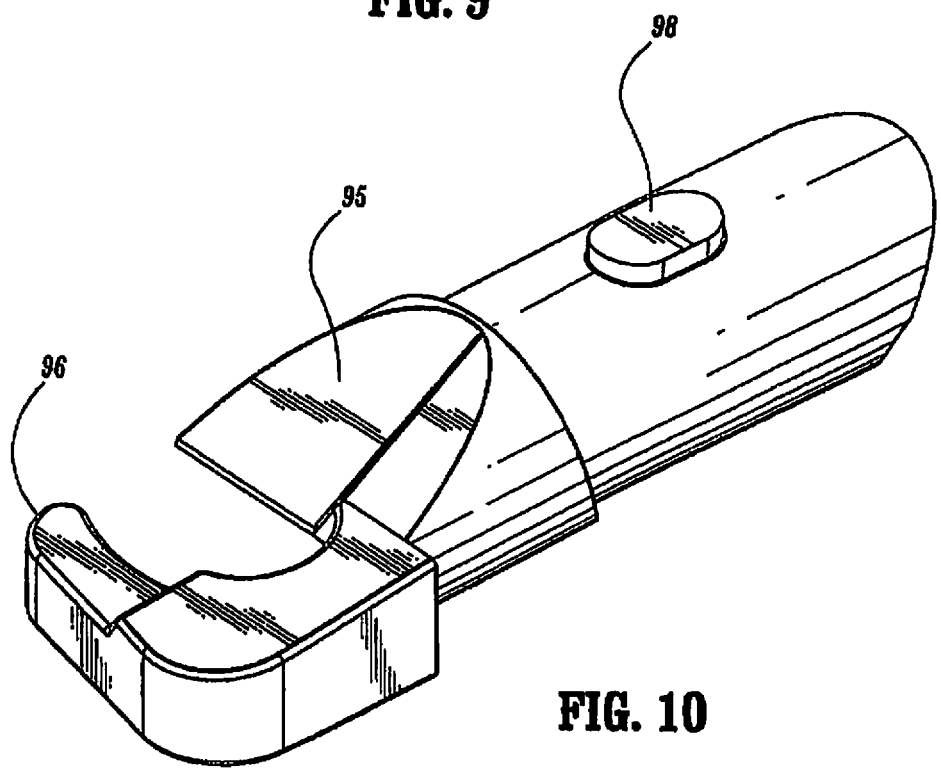
FIG. 10 is an isometric bottom view of the anvil of FIG. 9.

Referring now to FIGS. 4, 9 and 10, anvil 90 is shown having a distal end 92 and a proximal end 94. Distal end 92 includes a jaw 96 that at least partially is configured for the seating of clips 150 and defines a longitudinal slot 99. Proximal end 94 has a flat planar portion and defines a distally angled hole 97. A protuberance 98 is positioned in the vicinity of proximal end portion 94, and is configured to interface with a hole 141 defined in the distal end of anvil channel 140. Proximal portion 94 terminates with a beveled proximal edge 95. The abutting interface of bevel 95 with beveled portion 127 provides a stop or limit to the distal movement of feed rod 120. This limit at least partially controls the degree of compression applied by hammer 80 on anvil 90.

Figure 11:
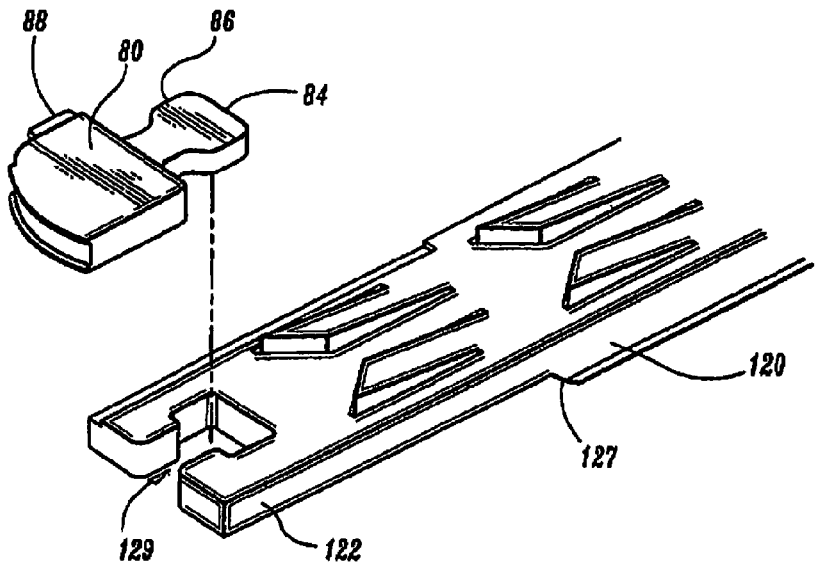
FIG. 11 is an isometric exploded view of a hammer and a feed rod of the apparatus of FIG. 1.
Figure 12:
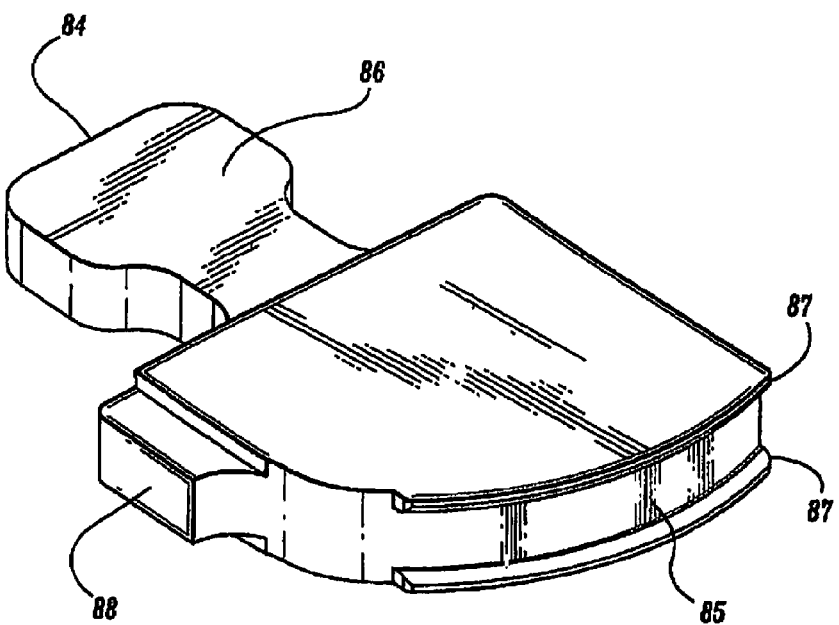
FIG. 12 is an enlarged isometric view of the hammer of FIG. 11.

In FIGS. 11 and 12, hammer 80 is illustrated with a proximal end 84 including a mating portion 86 configured to correspondingly engage with a slot 129 defined in distal end 122 of feed rod 120. Mating portion 86 is configured to interface with and transfer the drive force from feed rod 120 to hammer 80 independent of the rotational orientation of right angle clip applier apparatus 10 (see FIG. 4).

Hammer 80 includes a tongue portion 88 interfaces with a corresponding slot 99 of anvil 90 for assisting in the alignment and retention of hammer 80 during translation (see FIGS. 9 and 10). A face 85 correspondingly mates with jaw 96. In this embodiment, face 85 is generally convex and jaw 96 is concave, but hammer face 85 and jaw 96 can take any corresponding geometric shape depending upon the desired application and clip geometry. Hammer 80 also includes ridge portions 87 positioned at least partially on face 85 for the retention of clips (not shown) as they are compressed against jaw 96.

Figure 13:
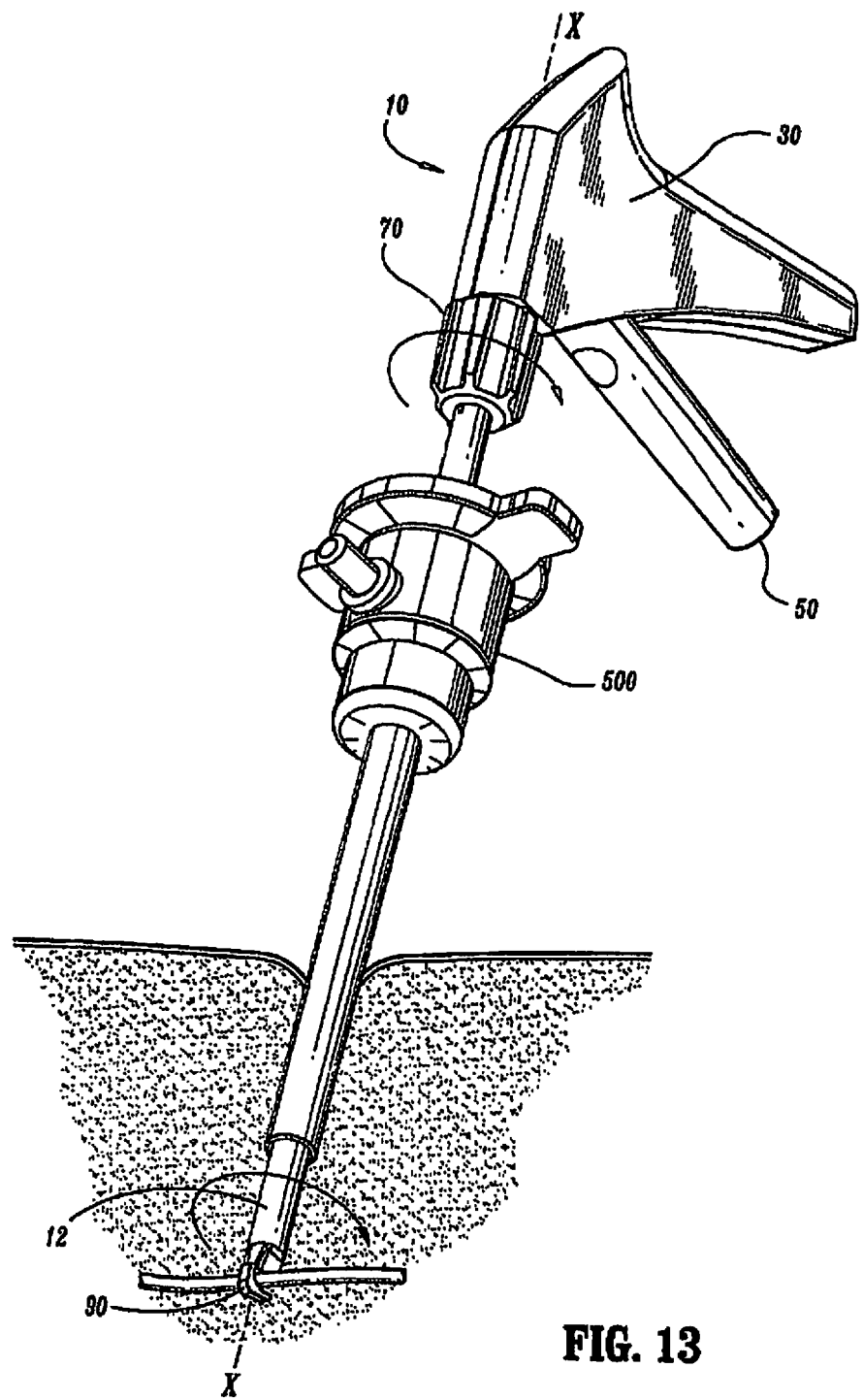
FIG. 13 is an isometric view of the apparatus of FIG. 1 in operation being employed through a trocar.

In FIG. 13, right angle clip applier apparatus 10 is shown in operation in conjunction with a trocar 500. Distal end 12 passes penetrates through and beyond the distal end of trocar 500. Right angle oriented anvil 90 is then positioned around the tissue portion and lever 50 is squeezed proximally to distally advance rotate, and form a first clip positioned at distal end 12 on the selected tissue portion. Distal end 12 can be rotated clockwise or counterclockwise without limit by turning rotation control knob 70 about the central longitudinal axis "X-X" without moving handle 30.

FIGS. 14-19 show clip applying mechanism 20 and advancing mechanism 25 in a pre-fired position. Clips 150 are positioned between cartridge 130 and feed rod 120 and in plane "x-y". Depending upon the configuration of clip applying mechanism 20, first clip 150 may be in transition from plane "x-y" to plane "X-Y" or at least partially in plane "X-Y".

Cartridge 130 and feed rod 120 are disposed in an opposing relatively slidable relationship with sequentially positioned elements 133 and 123 formed thereon, respectively. Elements 123 and 133, are formed as portions of feed rod 120 and cartridge 130 respectively and terminate in cantilevered and flexible beams 125 and 135, respectively. As best shown in FIG. 17, distal ends of flexible beams 125 and 135 are angled to correspond substantially with the angle of clips 150 when positioned for advancement. Elements 133 retain clips 150 in their respective positions after being advanced by the drive force applied to clips 150 by elements 123 of feed rod 120. Cartridge 130 and feed rod 120 are configured through their biased elements and other structural elements to retain clips 150 in their respective positions independent of the orientation of apparatus 10.

Referring now to FIGS. 20 and 21, a single actuation of lever 50 provides the drive force that advances feed rod 120, including elements 123 contacting clips 150, distally a controlled distance (see FIGS. 16 and 17) to advance clips 150 to the next distal element 133. The first or distal-most clip 150 in right angle clip applier apparatus 10 is translated by hammer 80 distally, transitioned from plane "x-y" to "X-Y" (FIG. 16) and rotated into position by the pivoting of one leg of first clip 150 about stop 138 (FIG. 8). The pivoting of distal-most clip 150 moves it from a first position generally aligned with central longitudinal axis "X-X" to a second position generally aligned with axis "Y-Y". As distal-most clip 150 rotates approximately 90.degree., jaw 96 guides the clip around a tissue portion upon which first clip 150 is to be applied.

Hammer 80 in conjunction with anvil 90 applies distal-most clip 150 along the central longitudinal axis "X-X" on the tissue portion.

Continued compression of lever 50 advances, compresses, and forms distal-most clip 150 on the tissue positioned therein. Releasing lever 50 then provides a drive force from return spring 100 (FIG. 3) that repositions hammer 80, feed rod 120, and swivel 110 proximally to the pre-fired position. Clips 150 previously advanced distally by elements 123 are retained in position by elements 133 of cartridge 130 as feed rod 120 slides proximally over clips 150 and elements 133. The distal-most clip 150 comes into contact with and is held in position by face 85 of hammer 80. Thus, right angle clip applying apparatus 10 can be operated through a trocar at any angle, clip applying mechanism 20 and advancing mechanism 25 are configured to operate from any direction, independent of gravity or any angle of operation.

Figure 22:
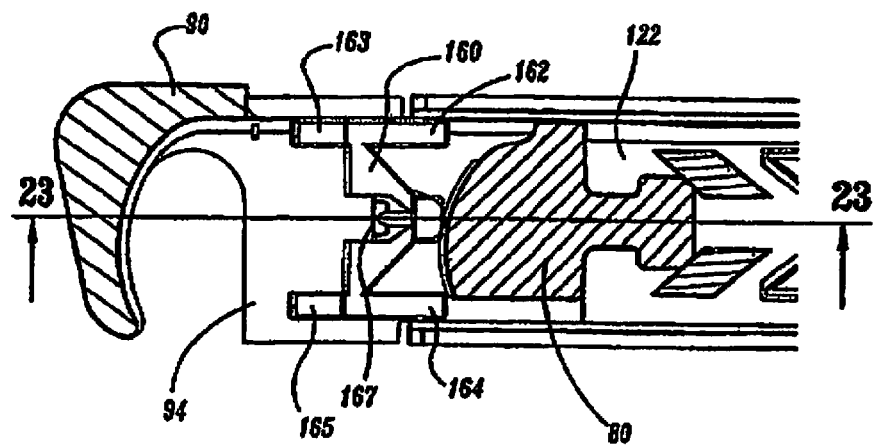
FIG. 22 is a top view of the anvil and hammer of FIG. 20 with the empty clip indicator positioned between the anvil and the hammer.
Figure 23:
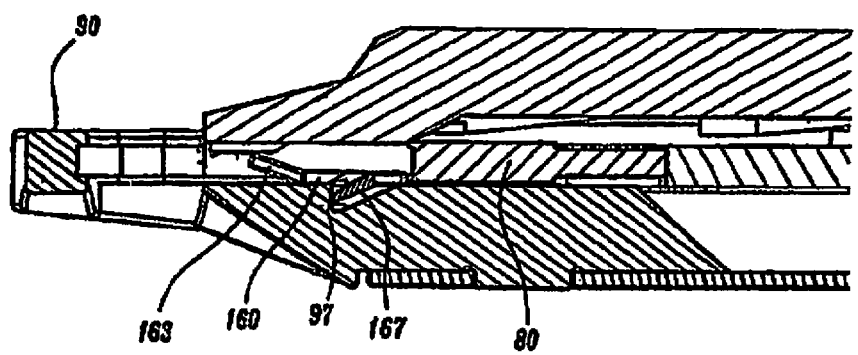
FIG. 23 is a cross-sectional side view of the anvil and hammer of FIG. 22 taken along section line 23-23.
Figure 24:
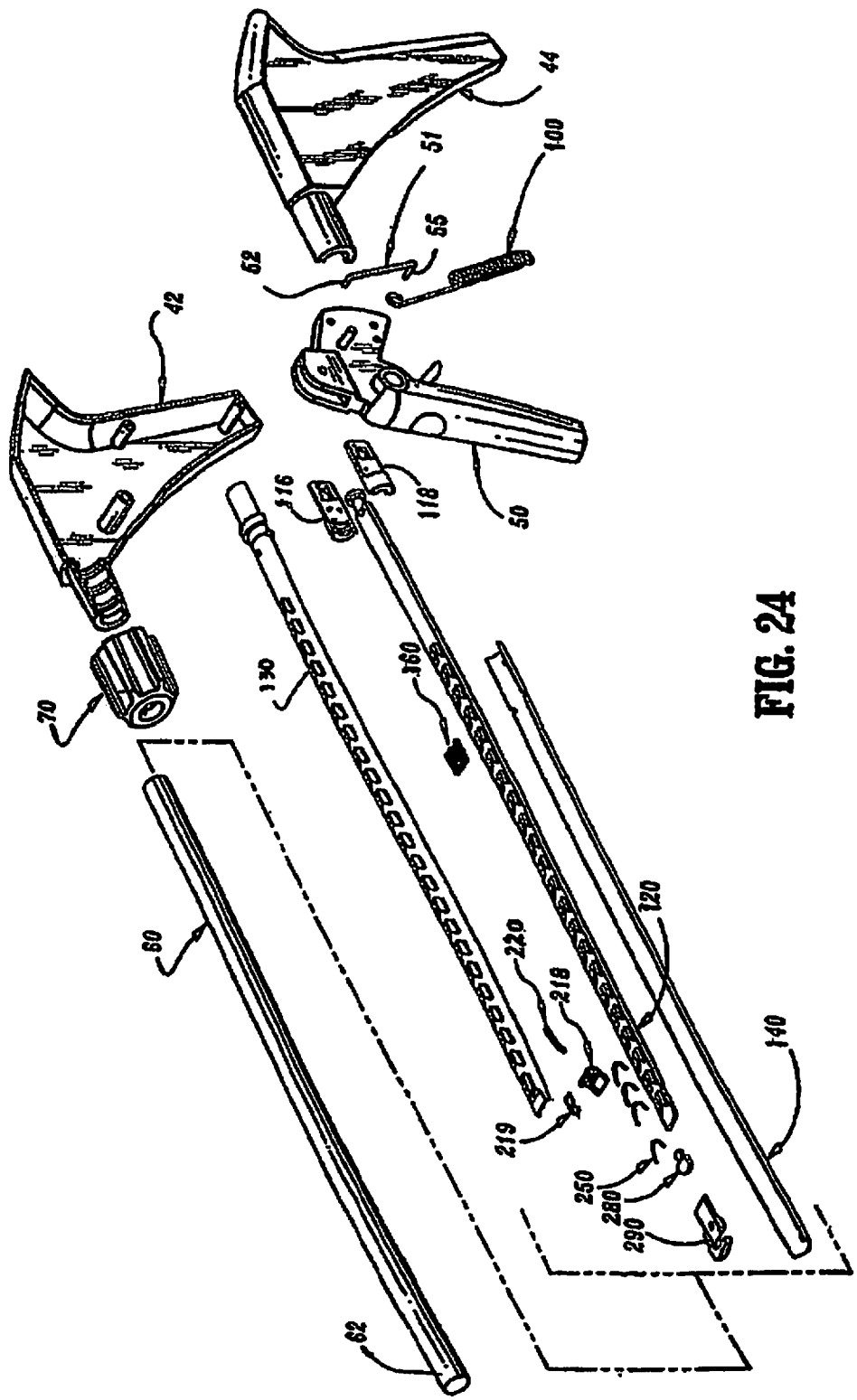
FIG. 24 is an isometric view of another embodiment of a right angle clip applier apparatus constructed in accordance with the present disclosure.
Figure 25:
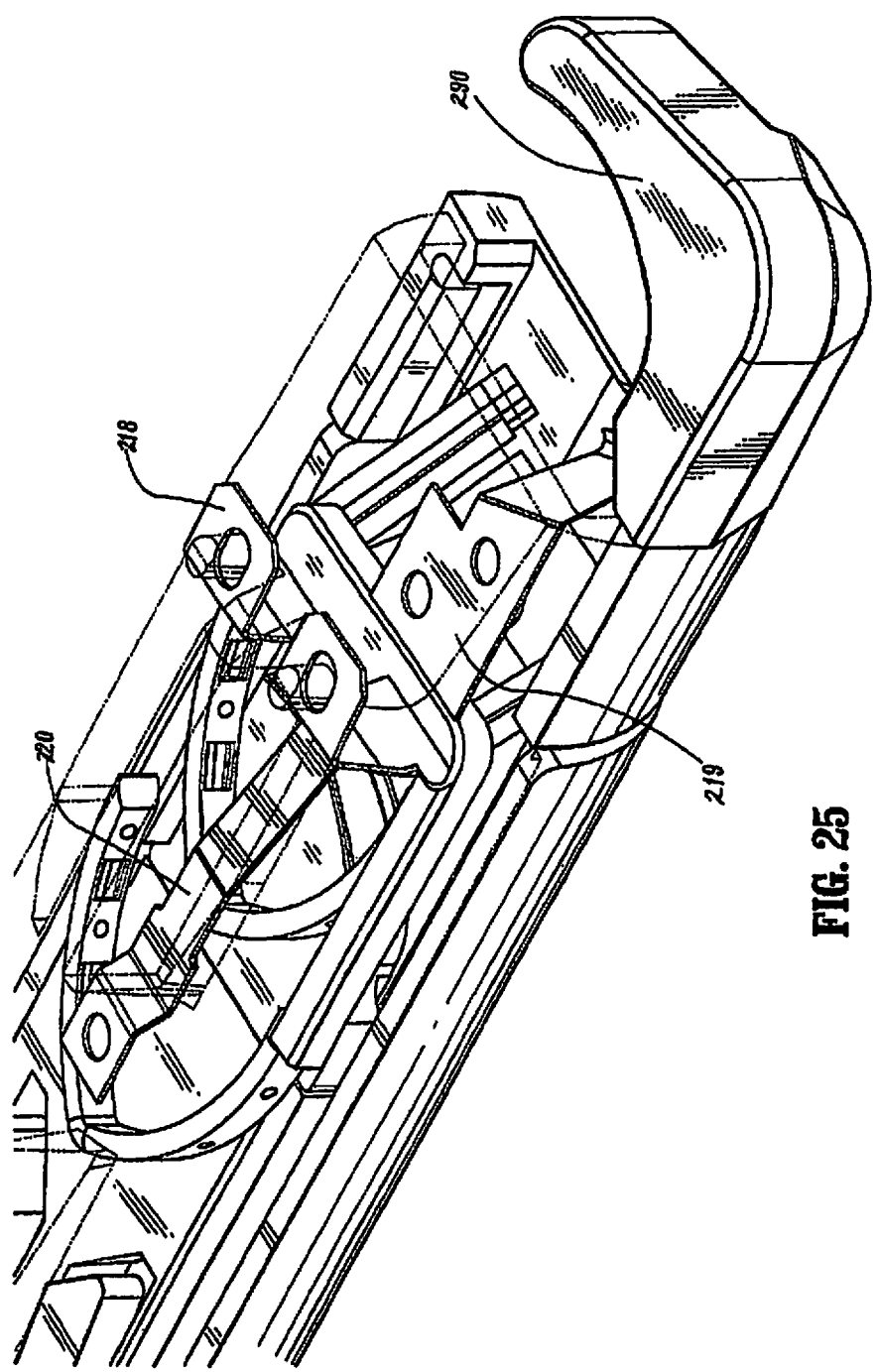
FIGS. 25-32 are various views of an alternative embodiment of the presently disclosed right angled clip applier which incorporates different structures to facilitate more controlled clip handling of the individual clips as they are advanced to the firing location.
Figure 26:
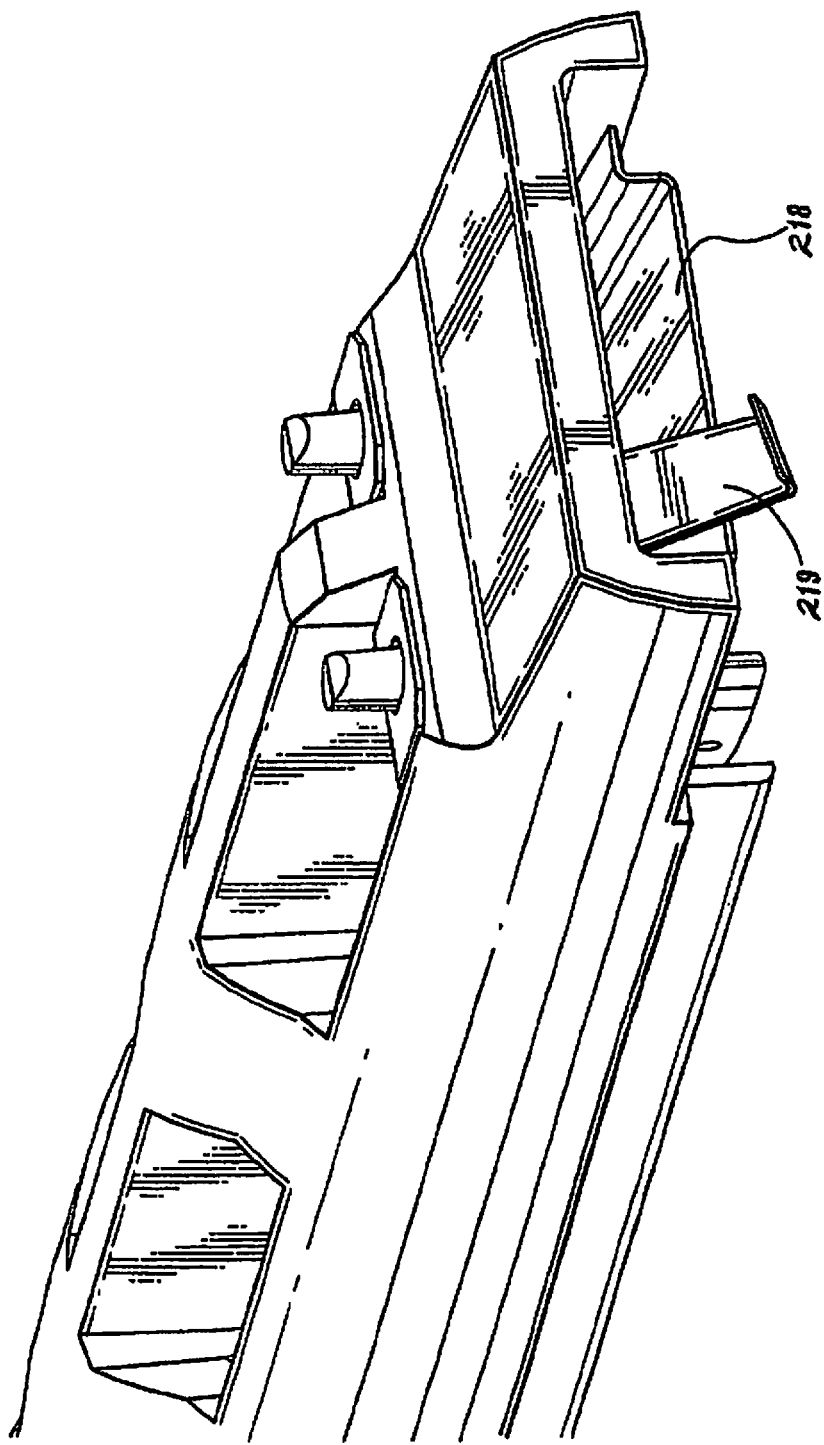
Figure 27:
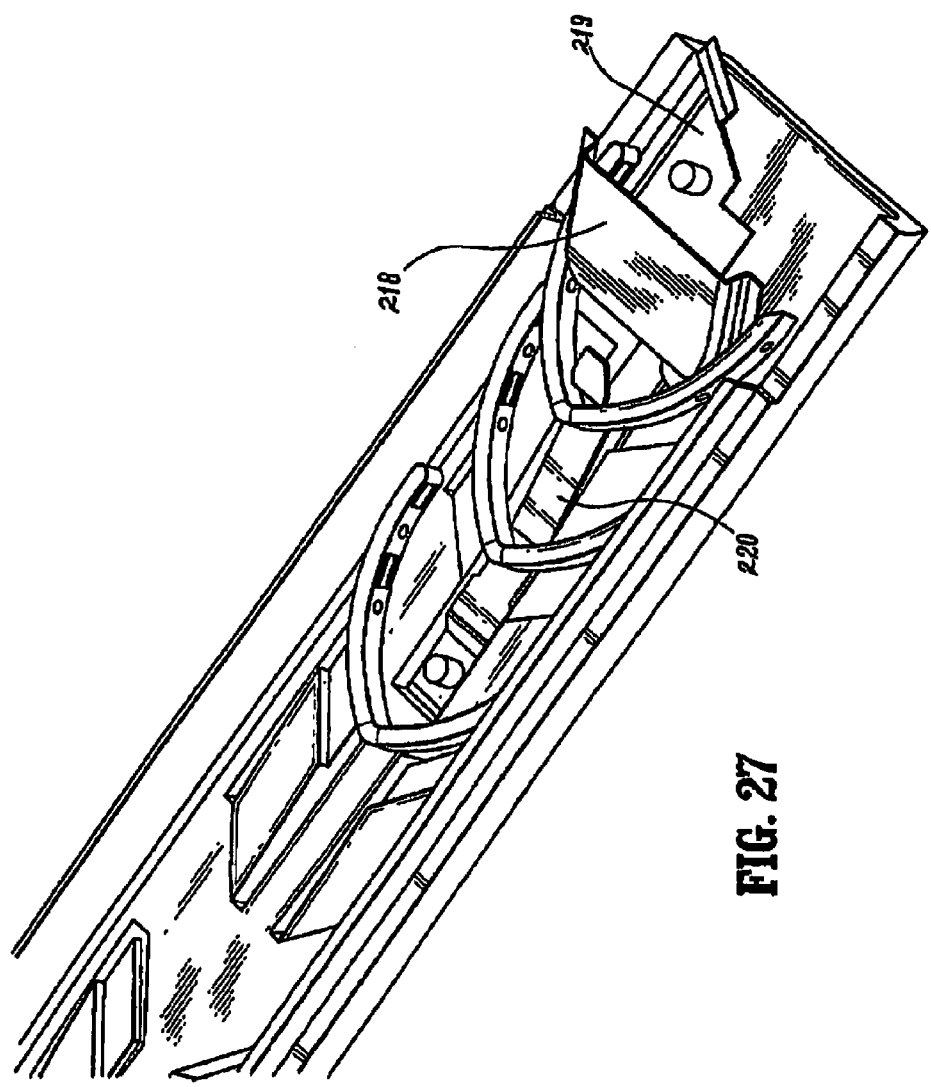
Figure 28:
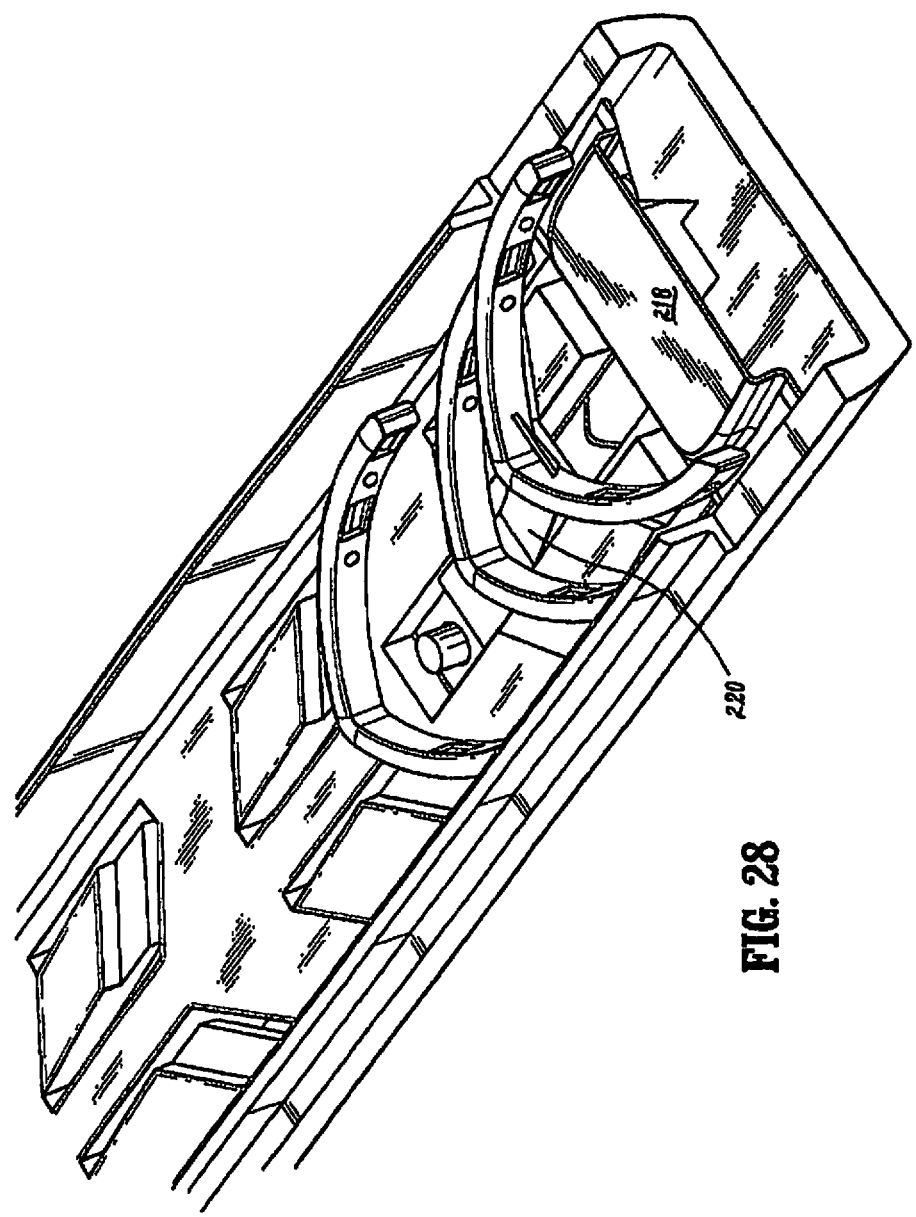
Figure 29:
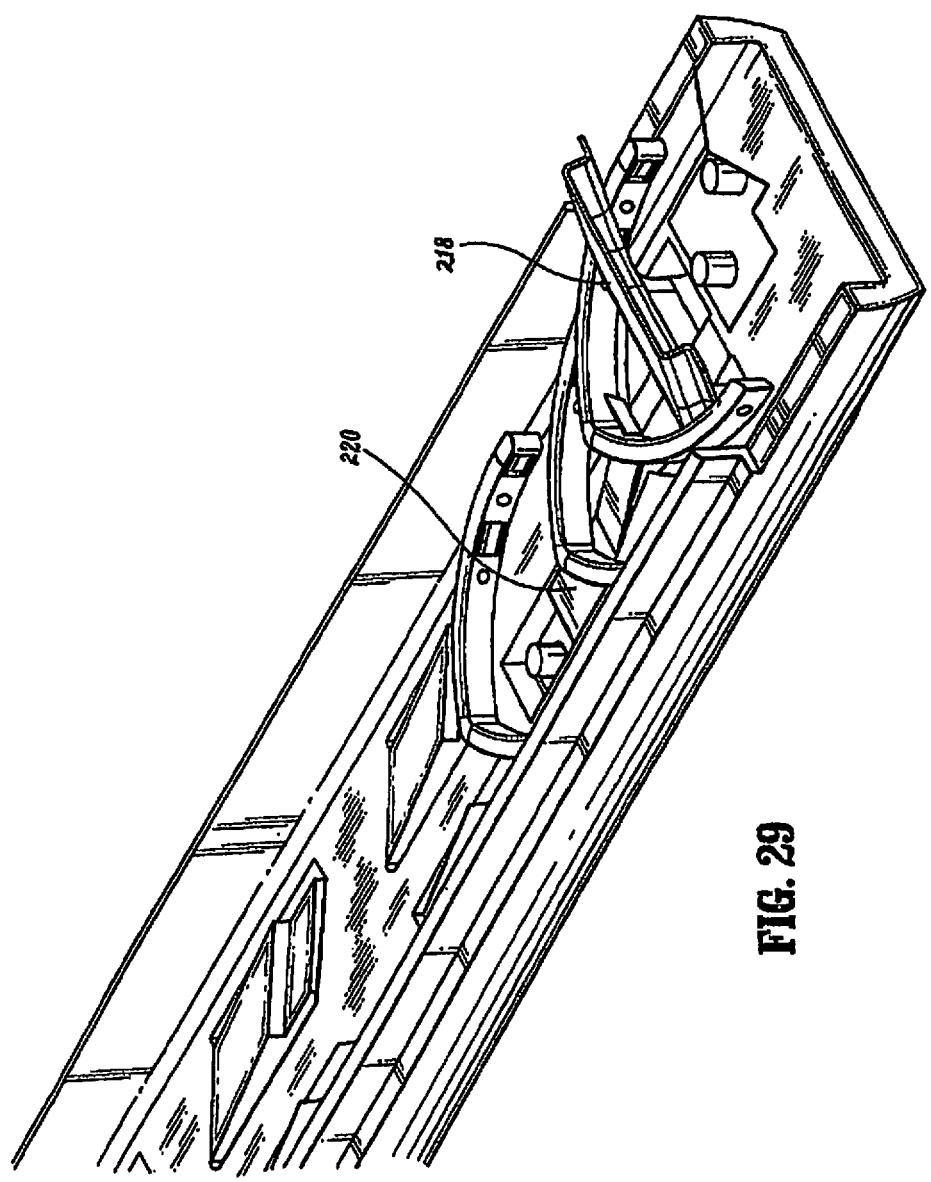
Figure 30:
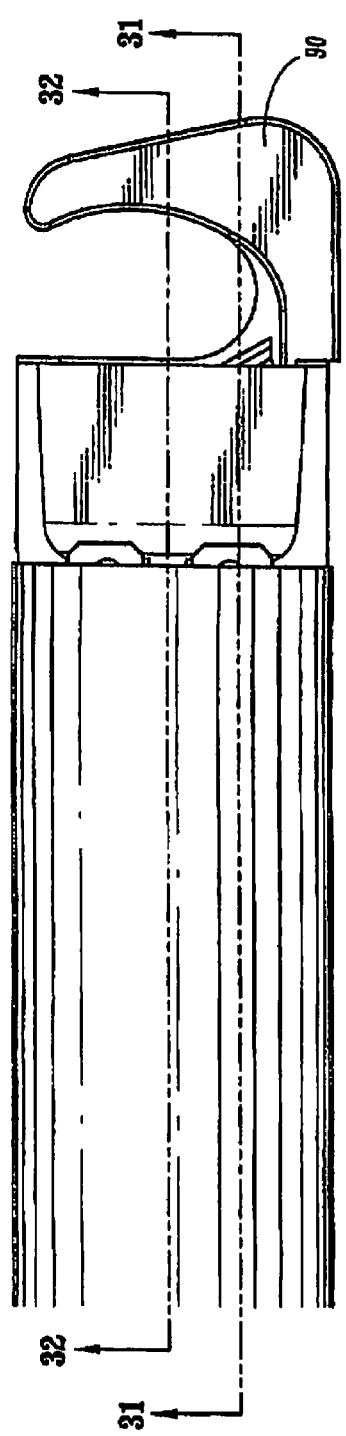
Figure 31:
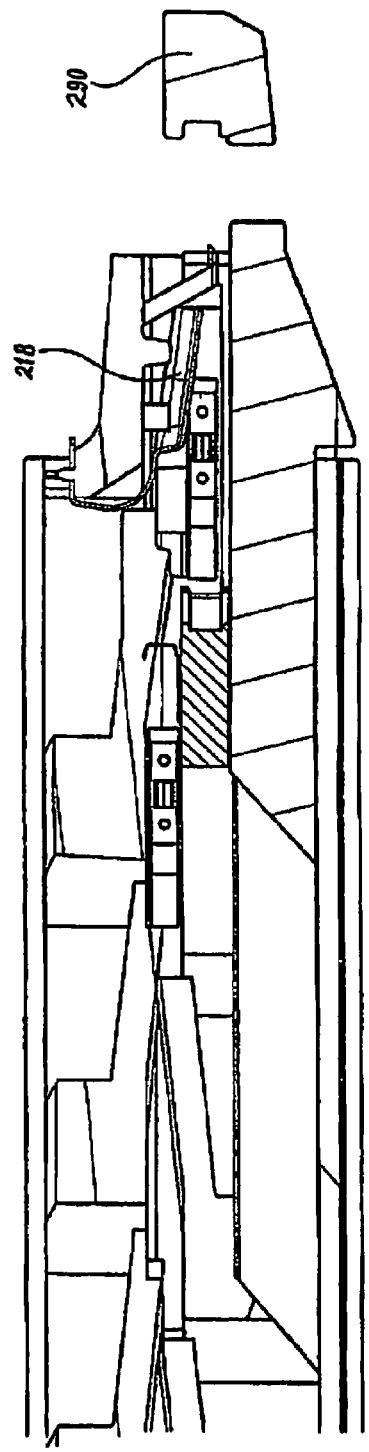
Figure 32:
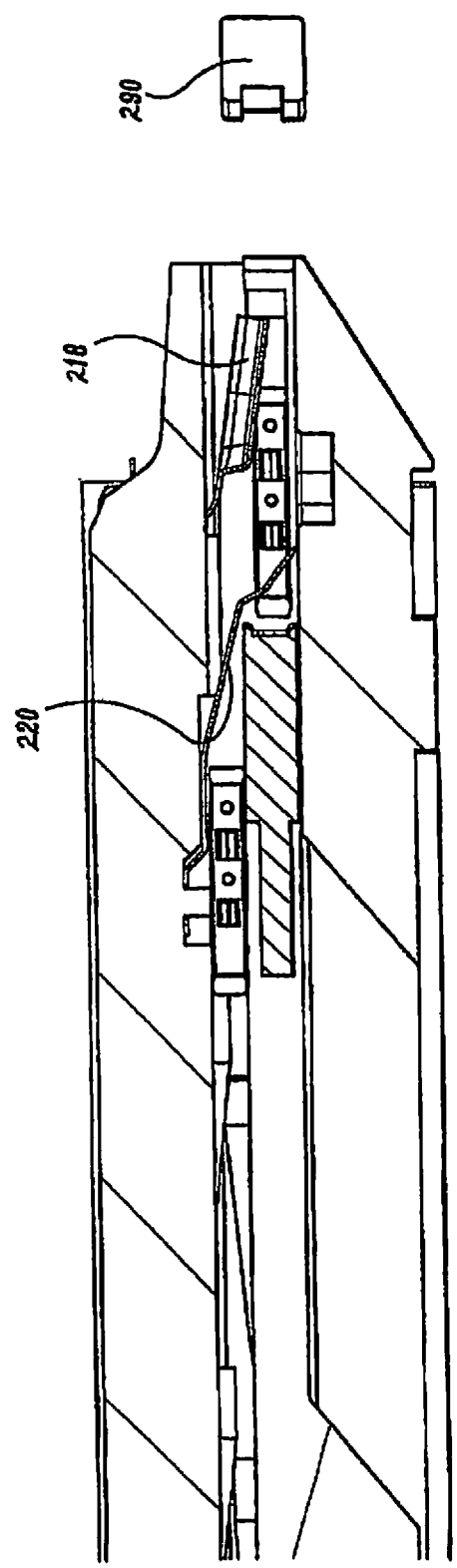

In FIGS. 22 and 23, empty clip indicator 160 is shown positioned on portion 94 between hammer 80 and anvil 90. Empty clip indicator 160 is positioned after all clips 150 or proximal to clips 150 on feed rod 120 (see FIG. 4). When empty clip indicator 160 portion 167 impacts with hole 97 (see FIGS. 6, 7, and 8), it precludes indicator 160 from advancing. Longitudinally aligned legs 162 and 164 similarly preclude empty clip indicator 160 from rotating within cartridge 130 about stop portion 138. At this point, empty clip indicator 160 blocks the drive force from progressing further and lever 50 can no longer be compressed signaling to the operator of right angle clip applier apparatus 10 that all of clips 150 have been exhausted. Empty clip indication 160 has the further advantageous effect of rendering the apparatus safe from unintentional applications.

Referring now to FIGS. 24-32, an alternative embodiment of the presently disclosed right angled clip applier incorporates different structures to facilitate more controlled clip handling of the individual clips 250 as they are advanced to the firing location. The clip applier illustrated in FIGS. 24-32 is another embodiment of clip applier 10 (FIG. 4) having a handle 30, cartridge 130, outer tube 60, and anvil channel 140. A spring leaf 220 is provided to ensure that, as the hammer 280 pulls more rearward back toward the proximal end of the instrument, the vertex of the clip 250 is pushed down flush against the anvil 290. On progressive actuation of the firing trigger, the distal-most clip 250 then gets advanced and more fully contacts a spring such as clip whip spring 218, which is a larger spring than spring leaf 220 and includes a formed portion to bias against the proximal end of the clip 250. The function of the clip whip spring 218 is to centralize each clip 250 as it is advanced into firing position so that the chamfered clip portion contacts the pivot point every time on the anvil 290. A clip rotation spring 219 functions to ensure that the clip 250, not the chamfered-side, fully contacts the rotation clip spring 219 in the anvil 290, and follows it all the way through, hugging it tightly during the progressive actuation of the trigger. In this manner, the unit can be actuated while actually on a vessel.

The whole function of spring leaf 220 is that once the hammer 280 is fully forward forming a clip 250, the next clip 250 is in a ready position, part of the open end of the clip 250 is already in contact with the clip-whip 218. The vertex of that clip 250 is in contact with the spring leaf 220 as the hammer 280 pulls back, that spring leaf 220 ensures that the clip's vertex is pushed down flush against the anvil 290. So on the next actuation of the hammer 280 coming forward to advance the next clip 250, it will fully contact that vertex of the clip 250 and not right underneath of it.

The rotation clip 219 is angled clip which is very closely positioned to facilitate its function of ensuring that as the clip to be fired next is exiting the cartridge assembly 130 and into the anvil 250, it is angled such that it always forces the open end of the clip 250 into the clip track, right next to the anvil 290. Thus, ensuring that 1) the clip 250 does contact the anvil 290 and the clip track and follows the track all the way around to forming, but 2) also ensuring that the clip 250 will not poke through a vessel, rather it will go underneath the vessel.

Although the illustrative embodiments of the present disclosure have been described herein with reference to the accompanying drawings, it is to be understood that the disclosure is not limited to those precise embodiments and that various other changes and modifications may be affected therein by one skilled in the art without departing from the scope or spirit from the disclosure. All such changes and modifications are intended to be included within the scope of the appended claims.

What is claimed is:

1. A clip applier comprising:
a clip applying mechanism configured and dimensioned to advance a plurality of clips along an axis parallel to a central longitudinal axis of the clip applier in a distal direction;
a hammer in direct contact with the clip applying mechanism;
an anvil cooperatively engageable with the hammer;
a stop structure positioned adjacent a distal portion of the clip applying mechanism; and
an empty clip indicator located proximally of a proximal-most clip in the plurality of clips, wherein translation of the clip applying mechanism advances the empty clip indicator in the distal direction such that the empty clip indicator engages the stop structure to prevent continued distal advancement of the clip applying mechanism, and thereby disable the clip applying mechanism the empty clip indicator including two legs and a cross member.

2. The clip applier of claim 1 further including a handle assembly operatively connected to the clip applying mechanism, the handle assembly being actuable to generate a drive force.

3. The clip applier of claim 1, wherein the clip applying mechanism includes a feed rod translatable along the central longitudinal axis of the clip applier, a distal portion of the clip applying mechanism being fixed relative to the feed rod.

4. The clip applier of claim 3, wherein the hammer is in direct contact with the feed rod of the clip applying mechanism.

5. The clip applier of claim 1, wherein the clip applying mechanism further includes is cartridge configured and dimensioned to accommodate the plurality of clips.

6. The clip applier of claim 5, wherein the cartridge includes a stop formed at a distal end thereof configured and dimensioned to engage a distal-most clip in the plurality of clips to effectuate rotation of the distal-must clip for positioning about target tissue prior to firing of the clip applier.

7. The clip applier of claim 6, wherein the stop and the clips are configured and dimensioned such that the distal-most clip is rotated in a plane that is substantially parallel to the central longitudinal axis of the clip applier upon engagement with the stop.

8. The clip applier of claim 7, wherein the anvil and the hammer are cooperatively engageable to apply the distal-most clip to the target tissue at an angle of application transverse to the central longitudinal axis of the clip applier.

9. The clip applier of claim 1, wherein the empty clip indicator includes a body with a protrusion extending therefrom.

10. The clip applier of claim 9, wherein the protrusion and the stop structure are configured and dimensioned such that, subsequent to engagement of the protrusion and the stop structure, the protrusion is substantially aligned with the central longitudinal axis of the clip applier.

11. A clip applier comprising:
a clip applying mechanism rotatable about a longitudinal axis of the clip applier, the clip applying mechanism including a cartridge having a plurality of elements for retaining a plurality of clips;
a translatable feed rod slidingly engaged with the cartridge, the feed rod including a plurality of elements positioned thereon for distally advancing the plurality of clips;
a hammer in direct contact with the feed rod;
an anvil positioned to receive the clips, the anvil being configured and dimensioned to engage the hammer to apply a distal-most clip in the plurality of clips to target tissue;
a stop structure positioned adjacent a distal portion of the clip applying mechanism, the stop structure being fixed relative to translation of the feed rod; and
an empty clip indicator including at least one proximally extending leg aligned with the longitudinal axis, the empty clip indicator being located proximally of a proximal-most clip in the plurality of clips such that distal translation of the feed rod causes corresponding translation of the empty clip indicator, the empty clip indicator being, configured and dimensioned for engagement with the stop structure to prevent continued distal advancement of the feed rod to thereby disable the clip applying mechanism.

12. The clip applier of claim 11 further including a handle assembly operatively connected to the clip applying mechanism, the handle assembly being actuable to generate a drive force to advance the plurality of clips such that the distal-most clip engages the hammer.

13. The clip applier of claim 11, wherein the clip applying mechanism includes a distal portion fixed relative to the feed rod.

14. The clip applier of claim 11, wherein the cartridge includes a stop formed at a distal end thereof configured and dimensioned to engage the distal-most clip to effectuate rotation of the distal-most clip for positioning about the target tissue prior to firing of the clip applier.

15. The clip applier of claim 14, wherein the stop and the clips are configured and dimensioned such that the distal-most clip is rotated in a plane that is substantially parallel to a central longitudinal axis of the clip applier upon engagement with the stop.

16. The clip applier of claim 15, wherein the anvil and the hammer are configured and dimensioned for engagement such that the distal-most clip is applied to the target tissue at an angle transverse to the longitudinal axis.

17. The clip applier of claim 11, wherein the empty clip indicator and the stop structure are configured and dimensioned such that alignment of the at least one leg with the longitudinal axis is maintained upon engagement of the empty clip indicator with the stop structure.

18. A clip applier comprising:
a clip applying mechanism including a feed rod translatable along a central longitudinal axis, and a distal portion fixed relative to the translation or the feed rod, the feed rod being configured and dimensioned to distally advance a plurality of clips positioned therewith, wherein a clip is rotated relative to the distal portion in a plane that is substantially parallel to the central longitudinal axis prior to firing of the clip applier;
an anvil cooperatively engageable with a hammer positioned on the feed rod for applying a first clip at an angle of application transverse to the central longitudinal axis;
a stop structure positioned adjacent the distal portion of the clip applying mechanism; and
an empty clip indicator having a body with a protrusion extending therefrom, the empty clip indicator being located proximally of a proximal-most clip in the plurality of clips, wherein translation of the feed rod advances the empty clip indicator in a distal direction such that the protrusion engages the stop structure to prevent continued distal advancement of the feed rod and thereby disable the clip applying mechanism, wherein subsequent to engagement of the protrusion and the stop structure, the protrusion is substantially aligned with the central longitudinal axis the empty clip indicator including two legs and a cross member.

19. The clip applier of claim 18 further including a handle assembly operatively connected to the clip applying mechanism, the handle assembly being actuable to generate a drive force to advance the plurality of clips into engagement with the hammer.

20. The clip applier of claim 18, wherein the clip applying mechanism further includes a cartridge configured and dimensioned to accommodate the plurality of clips, the cartridge including a stop formed at a distal end thereof configured to engage a distal-most clip in the plurality of clips to effectuate rotation of the distal-most clip for positioning about target tissue prior to firing of the clip applier.

21. The clip applier of claim 1, wherein the configuration and dimensions of the empty clip indicator are different from those of the plurality of clips.

22. The clip applier of claim 11, wherein the configuration and dimensions of the empty clip indicator are different from those of the plurality of clips.

23. The clip applier of claim 18, wherein the configuration and dimensions of the empty clip indicator are different front those of the plurality of clips.

* * * * *